US008936926B2

(12) United States Patent
Hanzel et al.

(10) Patent No.: US 8,936,926 B2
(45) Date of Patent: *Jan. 20, 2015

(54) ACTIVE SURFACE COUPLED POLYMERASES

(75) Inventors: David Hanzel, Palo Alto, CA (US);
Jonas Korlach, Menlo Park, CA (US);
Paul Peluso, Hayward, CA (US);
Geoffrey Otto, Santa Clara, CA (US);
Thang Pham, Mountain View, CA (US);
David Rank, Palo Alto, CA (US);
Stephen Turner, Menlo Park, CA (US)

(73) Assignee: Pacific Biosciences of California, Menlo Park, CA (US)

( * ) Notice: Subject to any disclaimer, the term of this patent is extended or adjusted under 35 U.S.C. 154(b) by 1759 days.

This patent is subject to a terminal disclaimer.

(21) Appl. No.: 11/645,125

(22) Filed: Dec. 21, 2006

(65) Prior Publication Data

US 2010/0261247 A1     Oct. 14, 2010

Related U.S. Application Data

(60) Provisional application No. 60/753,515, filed on Dec. 22, 2005.

(51) Int. Cl.
*C12N 11/16* (2006.01)
*C12N 9/12* (2006.01)
*C12Q 1/68* (2006.01)

(52) U.S. Cl.
CPC ............ *C12Q 1/6837* (2013.01); *C12N 9/1252* (2013.01); *C12Q 1/6844* (2013.01); *C07K 2319/23* (2013.01)
USPC .......................................... 435/194; 435/174

(58) Field of Classification Search
None
See application file for complete search history.

(56) References Cited

U.S. PATENT DOCUMENTS

| 5,198,543 | A | 3/1993 | Blanco et al. |
| 5,576,204 | A | 11/1996 | Blanco et al. |
| 5,614,365 | A | 3/1997 | Tabor et al. |
| 5,736,373 | A | 4/1998 | Hamilton |
| 5,837,814 | A | 11/1998 | Shoseyou et al. |
| 5,972,603 | A | 10/1999 | Bedford et al. |
| 6,383,483 | B1 | 5/2002 | Collen |
| 6,607,883 | B1 | 8/2003 | Frey et al. |
| 6,917,726 | B2 | 7/2005 | Levene et al. |
| 7,205,106 | B1 | 4/2007 | Mirel et al. |
| 7,238,505 | B2 | 7/2007 | Hwang et al. |
| 7,270,951 | B1 * | 9/2007 | Stemple et al. .................. 435/6 |
| 7,292,742 | B2 | 11/2007 | Levene et al. |
| 7,560,254 | B2 | 7/2009 | Sood et al. |
| 7,777,013 | B2 | 8/2010 | Xu et al. |
| 2003/0044781 | A1 | 3/2003 | Korlach et al. |

FOREIGN PATENT DOCUMENTS

| WO | WO 00/53805 A1 | 9/2000 |
| WO | WO 02/29027 A1 | 4/2002 |
| WO | WO 02/086088 A2 | 10/2002 |
| WO | WO 2004/092331 A2 | 10/2004 |

OTHER PUBLICATIONS

Adelman et al. (2002) "Single Molecule Analysis of RNA Polymerase Elongation Reveals Uniform Kinetic Behavior." *Proceedings of the National Academy of Sciences, USA*, 99(21): 13538-13543.
Levene et al. (2003) "Zero-mode waveguides for single-molecule analysis at high concentrations." *Science*, 299(5607): 682-686.
Nilsson et al. (1997) "Heat-Mediated Activation of Affinity-Immobilized Taq DNA Polymerase." *BioTechniques* 22(4): 744-751.
Albert et al (2005) "Structural Basis for Mambrane Anchorage of Viral φ29 DNA during Replication." *The Journal of Biological Chemistry*, 280(52): 42486-42488.
Bernad et al. (2006) "The Highly Conserved Amino Acid Sequence Motif Tyr-Gly-Asp-Thr-Asp-Ser in α-like DNA Polymerases is Required by Phage φ29 DNA Polymerase for Protein-Primed Initiation and Polymerization." 87: 4610-4614.
Blanco and Salas (1996) "Relating Structure to Function in φ29 DNA Polymerase." *The Journal of Biological Chemistry*, 271(15): 8509-8512.
Blasco et al. (1990) "Structural and functional analysis of temperature-senditive mutants of the phage φ29 DNA polymerase." *Nucleic Acids Research*, 18(16): 4763-4770.
Blasco et al. (1992) "Primer Terminus Stabilization at the φ29 DNA Polymerase Active Site." *The Journal of Biological Chemistry*, 270(6): 2735-2740.
Blasco et al. (1992) "Structural and functional studies on φ29 DNA polymerase." *Chromosoma*, 102: S32-S38.
Blasco et al. (1992) "φ29 DNA Polymerase Active Site." *The Journal of Biological Chemistry*, 267(27): 19424-19434.
Blasco et al. (1992) "φ29 DNA Polymerase Active Site." *The Journal of Biological Chemistry*, 268(32) 24106-24113.
Bonnin et al (1999) "A Single Tyrosine Prevents Insertion of Ribonucleotides in the Eukaryotic-type φ29 DNA Polymerase." *The Journal of Molecular Biology*, 290: 241-251.
Defour et al. (2000) "An Aspartic Acid residue in TPR-1, a Specific Region of Protein-priming DNA Polymerase, is Required for the Functional Interaction with Primer Terminal Protein." *The Journal of Molecular Biology*, 304: 289-300.
Defour et al. (2003) "A Conserved Insertion in Protein-primed DNA Polymerases is Involved in Primer Terminus Stabilisation." *The Journal of Molecular Biology*, 331: 781-794.
DeVega et al. (1996) "Primer-terminus stabilization at the 3'-5' exonuclease active site of φ29 DNA polymerase. Involvement of two amino acid residues highly conserved in proofreading DNA polymerases." *The EMBO Journal*, 15(5): 1182-1192.
DeVega et al. (1997) "An Invariant Lysine Residue is Involved in Catalysis at the 3'5' Exonuclease Active Site of Eukaryotic-type DNA Polymerase." *The Journal of Molecular Biology*, 270: 65-78.
DeVega et al. (1998) "Mutational Analysis of φ29 DNA Polymerase Residues Acting as ssDNa Ligands for 3'-5' Exonucleoysis." *The Journal of Molecular Biology*, 279: 807-822.

(Continued)

*Primary Examiner* — Richard Hutson
(74) *Attorney, Agent, or Firm* — Quine Intellectual Property Law Group, P.C.; Monica Elrod-Erickson; Robert Reamey

(57) ABSTRACT

Active surface coupled polymerases, surfaces that include such polymerases, and methods of making and using surface-attached polymerases are provided.

20 Claims, 2 Drawing Sheets

(56) References Cited

OTHER PUBLICATIONS

DeVega et al. (1998) "φ29 DNA Polymerase Residue Ser[122], a Single-stranded DNA Ligand for 3'=5' Exonucleoysis, is Required to Interact with the Terminal Protein." *The Journal of Biological Chemistry*, 273(44): 28966-28977.

DeVega et al. (1999) "Processive Proofreading and the Spatial Relationship between Polymerase and Exonuclease Active Sites of Bacteriophage φ29 DNA Polymerase." *The Journal of Molecular Biology*, 292: 39-51.

DeVega et al. (2000) "Phage φ29 DNA Polymerase Residues Involved in the Proper Stabilisation of the Primer-terminus at the 3'-5' Exnuclease Active Site." *The Journal of Molecular Biology*, 304: 1-9.

Eisenbrandt et al. (2002) "φ29 DNA polymerase residue Try59, His61 and Phe69 of the highly conserved ExoII motif are essential for interaction with the terminal protein." *Nucleic Acids Research*, 30(6): 1379-1386.

Esteban et al. (1993) "Fidelity of φ29 DNA Polymerase." *The Journal of Biological Chemistry*, 268(4): 2719-2726.

Illana et al. (1998) "The RGD Sequence in Phage φ29 Terminal Protein Is Required for Interaction with φ29 DNA Polymerase." *Virology*, 248: 12-19.

Illana et al. (1999) "Phage φ29 Terminal Protein Residues Asn[80] and Try[82] Are Recognition Elements of the Replication Origins." *The Journal of Biological Chemistry*, 274(21): 15073-15079.

Inoue et al. (2006) "Improvements of rolling circle amplification (RCA) efficiency and accuracy using *Thermus thermophilus* SSB mutant protein." *Nucleic Acids Research*, 34(9): e69.

Kamtekar et al. (2004) "Insights into Strand Displacement and Processivity from the Crystal Structure of the Protein-Prined DNA Polymerase of Bacteriophage φ29." *Molecular Cell*, 16: 609-618.

Kamtekar et al. (2006) The φ29 DNA polmerase protein-primer structure suggests a model for the initiation to elongation transition. *The EMBO Journal*, 25(6): 1335-1343.

Longás et al. (2006) "Functional characterization of highly processive protein-primed DNA polymerase from phages Nf and GA-1, endowed with a potent strand displacement capacity." Nucleic Acids Research, 34(20): 6051-6063.

Méndez et al. (1994) "Primer-terminus Stabilization at the φ29 DNA Polymerase Active Site." *The Journal of Biological Chemistry*, 269(47): 30030-30038.

Méndez et al. (1997) "Protein-primed DNA replication: a transition between two modes of priming by a unique DNA polymerase." *The EMBO Journal*, 16(9): 2519-2527.

Pérex-Arnaiz et al. (2006) "Invlovement of φ29 DNA polymerase thumb subdomain in the proper coordination of synthesis and degradation during DNA replication." *Nucleic Acids Research*, 34(10): 3107-3115.

Rodríguez et al. (2003) "φ29 DNA Polymerase Residue Phe128 of the Highly Conserved (S/T)Lx$_2$h Motif is Required for a Stable and Functional Interaction with the Terminal Protein." *The Journal of Molecular Biology*, 325: 85-97.

Rodríguez et al. (2004) "φ29 DNA Polymerase—Terminal Protein Interaction, Involvement of Residues Specifically Conserved Among Protein-primed DNA Polymerases." *The Journal of Molecular Biology*, 337: 829-841.

Rodríguez et al. (2005) "A specific subdomain in φ29 DNA poymarase confers both processivity and strand-displacement capacity." *The Proceedings of the National Academy of Sciences, USA*, 102: 6407-6412.

Saturno et al. (1995) "A Novel Kinetic Analysis to Calculate Nucleotide Affinity of Proofreading DNA Polymerases." *The Journal of Biological Chemistry*, 270(52): 31235-31243.

Saturno et al. (1997) "φ29 DNA Polymerase as a Residue Lys383, Invariant at Motif B of DNA-dependent Polymerases, is Involved in dNTP Binding." *The Journal of Molecular Biology*, 269: 313-325.

Saturno et al. (1998) "Role of the First Asparate Residue of the 'YxDTDS' Motif of φ29 DNA Polymerase as a Metal Ligand during both TP-primed and DNA-primed DNA Synthesis." *The Journal of Molecular Biology*, 283: 633-642.

Soengas et al. (1992) "Site-directed mutagenesis at the Exo III motif of φ29 DNA polymerase; overlapping and strand-displacement activities." *The Embo Journal*, 11(11): 4227-4237.

Steitz (2006) "Visualizing polynucleotide polymerase machines at work." *The EMBO Journal*, 25(15): 3458-3468.

Truniger et al. (2002) "A positively charged residue of φ29 DNA polymerase, highly conserved in DNA polymerase from families A and B, is involved in binding the incoming nucleotide." *Nucleic Acids Research*, 30(7): 1483-1492.

Truniger et al. (2003) "φ29 DNA Polymerase Residue Leu[384], Highly Conserved in Motif B of Eukaryotic Type DNA Replicases, Is Involved in Nucleotide Insertion Fidelity." *The Journal of Biological Chemistry*, 278(35): 33482-33491.

Truniger et al. (2004) "Function of the C-terminus of φ29 DNA polymerase in DNA and terminal protein binding." *Nucleic Acids Research*, 32(1): 361-370.

Truniger et al. (2005) "Involvement if the 'linker' region between the exonuclease and polymerization domains of φ29 DNA polymerase in DNA and TP binding." *Gene*, 348: 89-99.

Alba (2001) "Protein Family Review: Replicative DNA Polymerases." *Genome Biology* 2(1): reviews 3002.1-3002.4.

Augustin et al. (2001) "Progress Towards Single-molecule Sequencing: Enzymatic Synthesis of Nucleotide-specifically Labeled DNA." *Journal of Biotechnology*, 86(3): 289-301.

Blanco et al. (1995) "Mutational Analysis of Bacteriophage Phi 29 DNA Polymerase." *Methods of Enzimol.* 262: 283-294.

Blasco et al. (1993) "Phi 29 DNA Polymerase Active Site. Residue ASP249 of Conserved Amino Acid Motif 'Dx2SLYP' is Critical for Synthetic Activities." *J. Biot Chem.*, 268(32): 24106-13.

Blaso et al. (1993) "Phi 29 DNA Polymerase Active Site. The Conserved Amino Acid Motif 'Kx3NSxYG' is Involved in Template-primer Binding and dNTP Selection." *The Journal of Biological Chemistry*, 268(22): 16783-16770.

Brueggemeier et al. (2003) "Protein-acrylamide Copolymer Hydrogels for Array-based Detection of Tyrosine Kinase Activity from Cell Lysates." *Biomacromolecules*, 6(5): 2765-2775.

Burgers et al. (2001) "Eukaryotic DNA Polymerases: Proposal for a Revised Nomenclature." *The Journal of Biological Chemistry*, 276(47): 43487-43490.

Esteban et al. (1994) "3'-->5' Exonuclease Active Site of Phi DNA Polymerase. Evidence Favoring a Metal Ion-assisted Reaction Mechanims." *The Journal of Biological Chemistry*, 269(5): 31946-31954.

Gardner and Jack (1999) "Determinants of Nucleotide Sugar Recognition in an Archaeon DNA Polymerase." *Nuclaid Acids Research*, 27(12): 2545-2553.

Gardner et al. (2004) "Comparative Kinetics and Nucleotide Analog Incorporation by Vent DNA Polymerase." *The Journal of Biological Chemistry*, 279(12): 11834-11842.

Giller et al. (2003) "Incorporation of Reporter Molecule-labeled Nucleotides by DNA Polymerases. I. Chemical Synthesis of Various Reporter Group-labeled 2'-deoxyribonucleoside-5'-triphosphates." *Nucleic Acids Research*, 31(10): 2630-2635.

Hubscher et al. (2002) "Eukaryotic DNA Polymerases." *Annual Review of Biochemistry*, 71: 133-163.

Meijer et al. (2002) "Phi 29 Family of Phages." *Microbiology and Molecular Biology Reviews*, 65(2): 261-287.

Nieba et al. (1997) "BIACORE Analysis of Histidine-tagged Proteins Using a Chelating NTA Sensor Chip." *Analytical Biochemistry*, 252: 217-228.

Ried et al. (1992) "Simultaneous Visualization of Seven Different DNA Probes by in Situ Hybridization Using Combinatorial Fluorescence and Digital Imaging Microscopy." *Proceedings of the National Academy of Sciences, USA*, 89(4): 1383-1392.

Steitz (1999) "DNA Polymerases: Structural Diversity and Common Mechanisms." *The Journal of Biological Chemistry*, 274(25): 17395-17393.

Tonon et al. (2000) "Spectral Karyotyping Combined with Locus-specific FISH Simultaneously Defines Genes and Chromosomes Involved in Chromosomal Translocations." *Genes, Chromosomes & Cancer*, 27: 418-423.

Truniger et al. (2004) "Two Positively Charged Residues of φ29 DNA Polymerase, Conserved in Protein-primed DNA Polymerases, are

(56) References Cited

OTHER PUBLICATIONS

Involved in Stabilisation of the Incoming Nucleotide." The Journal of Molecular Biology, 335(2): 481-494.

Yu et al. (1994) "Cyanine dye dUTP Analogs for Enzymatic Labeling of DNA Probes." *Nucleic Acids Research*, 22(15): 3226-3232.

Zhu and Waggoner (1997) "Molecular Mechanism Controlling the Incorporation of Fluorescent Nucleotides into DNA by PCR." *Cytometry*, 2: 206-211.

Zhu et al. (1994) "Directly Labeled DNA Probes Using Fluorescent Nucleotides with Different Length Linkers." *Nucleic Acids Research*, 22(16): 3418-3422.

Gunneriusson et al. (1999) "Affinity maturation of a Taq DNA polymerase specific affibody by helix shuffling," *Protein Engineering*, 12(10):873-878.

Nilsson et al. (1996) "Multiple affinity domains for the detection, purification and immobilization of recombinant proteins," *J. Mol. Recognition*, 9(5-6):585-594.

Nilsson et al. (1997) "Affinity fusion strategies for detection, purification, and immobilization of recombinant proteins," *Protein Expression and Purification*, 11:1-16.

Gerlach et al. (2001) "Purification and Characterization of polκ, a DNA Polymerase Encoded by the Human DINB1 Gene." *The Journal of Biological Chemistry*, 276(1): 92-98.

Shapero et al. (2001) "SNP Genotyping by Multiplexed Solid-Phase Amplification and Fluorescent Minisequencing." *Genomic Research*, 11: 1926-1934.

Stano et al. (2005) "DNA synthesis provides the driving force to accelerate DNA unwinding by a helicase." *Nature Letters*, 435: 370-373.

Westin et al. (2000) "Anchored multiplex amplification on a microelectronic chip array." *Nature Biotechnology*, 18: 199-204.

Miyazaki et al. (2005) "Efficient Immobilization of Enzymes on Microchannel Surface Through His-Tag and Applications for Microreactor." *Protein and Peptide Letters*, 12(2): 207-210.

Ngo et al. (1994) "The Protein Folding Problem and Tertiary Structure Prediction." Chapter 14, Birkhauser, Boston, MA pp. 433 & 492-495.

Butz et al. (2004) "Detection of allelic variations of human gene expression by polymerase colonies." *BMC Genetics*, 5(3): 1-5.

Nilsson et al. (1997) "Heat-Mediated Activation of Affinity-Immobilized Taq DNA Polymerase." *Bio Techniques*, 22: 744-751.

Office Action dated May 13, 2011 for related application No. AU 2006331512.

Office Action dated May 24, 2013 for related application No. CA 2,633,476.

\* cited by examiner

ACTIVE SURFACE COUPLED POLYMERASES

CROSS-REFERENCE TO RELATED APPLICATIONS

This application is a non-provisional utility patent application claiming priority to and benefit of the following prior provisional patent application: U.S. Ser. No. 60/753,515, filed Dec. 22, 2005, entitled "ACTIVE SURFACE COUPLED POLYMERASES" by David Hanzel et al., which is incorporated herein by reference in its entirety for all purposes.

FIELD OF THE INVENTION

The invention relates to active surface coupled polymerases and surfaces that include such polymerases. Methods of making and using surface-attached polymerases are also described.

BACKGROUND OF THE INVENTION

DNA polymerases replicate the genomes of living organisms. For a review of polymerases, see, e.g., Hübscher et al. (2002) EUKARYOTIC DNA POLYMERASES *Annual Review of Biochemistry* Vol. 71: 133-163; Alba (2001) "Protein Family Review: Replicative DNA Polymerases" *Genome Biology* 2(1):reviews 3002.1-3002.4; and Steitz (1999) "DNA polymerases: structural diversity and common mechanisms" *J Biol Chem* 274:17395-17398.

In addition to a central role in biology, DNA polymerases are also ubiquitous tools of biotechnology. They are widely used, e.g., for reverse transcription, amplification, labeling, and sequencing, all of which are central technologies for a variety of applications, such as sequencing, nucleic acid amplification (e.g., PCR), cloning, protein engineering, diagnostics, molecular medicine and many others. The formats in which DNA polymerases are used vary widely, but generally the polymerase is present in solution when it is active. Useful formats include nucleic acid amplification and/or sequencing in automated amplification and/or sequencing devices, microtiter plates, microfluidic devices, PCR machines, and many others.

Active DNA polymerases captured to a solid phase, e.g., for use in solid phase DNA amplification, have not generally been available. Indeed, surface immobilization has been shown to disrupt DNA polymerase activity, in at least some settings. For example, affinity immobilization of Taq DNA polymerase has been used to suppress DNA polymerase activity until the polymerase is released from affinity capture (by application of high temperature). See, e.g., Nilsson et al. (1997) "Heat-Mediated Activation of Affinity-Immobilized Taq DNA Polymerase" *BioTechniques* 22:744-751.

An RNA-polymerase system in which an active RNA polymerase is coupled to a surface through an anti-HA antibody binding to an HA-tagged polymerase is described by Adelman et al. (2002) "Single Molecule Analysis of RNA Polymerase Elongation Reveals Uniform Kinetic Behavior" *PNAS* 99(21):13538-13543. This RNA polymerase was labeled at the N-terminus with a His-6 tag (for purification of the enzyme prior to attachment) and a C-terminal HA tag for binding to a surface. The anti-HA antibody was non-specifically adsorbed on the surface, which was additionally blocked with milk protein to reduce non-specific binding. The assay that this system was applied to is rather specialized and complex, involving detecting the physical forces exerted by an RNA polymerase during transcription. Applicability of this RNA polymerase system to other enzymes and to general topics such as detecting amplification products in general for high-throughput sequencing, labeling and amplification methods is unclear. For example, RNA polymerase is much slower than many DNA polymerase (5 bp/s vs. about 750 bp/s maximum in vitro), and RNA pols cannot easily be used for DNA amplification, SNP detection or the like.

While there are many solution phase applications of DNA polymerases that are useful, further applications in which the polymerase is active on a solid surface would be desirable. For example, the ability to fix the polymerase to a selected location on a surface could permit the creation of arrays of DNA polymerases, the activity of which could be detected using available array reader technologies. Furthermore, the ability to position a polymerase on a surface could permit single-molecule analysis of DNA products at the site on the surface where the DNA polymerase resides. This, in turn, would permit real-time monitoring of polymerase reactions, e.g., as in real time PCR (RT-PCR) or real-time sequencing. The present invention provides these and other features that will be apparent upon review of the following.

SUMMARY OF THE INVENTION

The invention includes DNA polymerases that can be coupled to a surface, without substantial loss of activity. DNA polymerases can be coupled to the surface through multiple surface coupling domains, which act in concert to increase binding affinity of the polymerase for the surface and to orient the polymerase relative to the surface. For example, the active site can be oriented distal to the surface, thereby making it accessible to a polymerase substrate (template, nucleotides, etc.). This orientation also tends to reduce surface denaturation effects in the region of the active site. In a related aspect, activity of the enzyme can be protected by making the coupling domains large, thereby serving to further insulate the active site from surface binding effects. Accordingly, isolated and/or recombinant polymerases comprising surface binding domains, surfaces with active polymerases bound to them and methods of coupling enzymes to surfaces are all features of the invention. Methods of amplifying template nucleic acids using surface-bound polymerases are also provided.

Accordingly, in a first aspect, an isolated or recombinant DNA polymerase is provided. The polymerase includes an active site and an artificial or recombinant surface coupling domain distal to the active site.

The polymerase can be homologous to any available polymerase and can include features in addition to the surface coupling domain, such as a deletion in one or more editing domains of the polymerase. For example, the polymerase optionally displays reduced or eliminated (e.g., 3'-5') exonuclease activity (useful in a variety of sequencing applications where common polymerase editing functions complicate sequencing). Alternately, the polymerase optionally displays exonuclease activity (useful, e.g., where high-fidelity DNA amplification is desirable). The polymerase can be homologous to, e.g., a Taq polymerase, an exonuclease deficient Taq polymerase, an *E. coli* DNA Polymerase 1, a Klenow fragment, a reverse transcriptase, a wild type Φ29 polymerase, a Φ29 related polymerase, such as an exonuclease deficient Φ29 polymerase or another modified Φ29 related polymerase, a T7 DNA Polymerase, a T5 DNA Polymerase, and/or the like.

In certain embodiments, the DNA polymerase has features useful in incorporating nucleotide analogues, e.g., modifications of the active site region that permit entry and/or facilitate binding of the nucleotide analogues at the active site. Examples include DNA polymerases homologous to a wild-type Φ29 DNA polymerase that include a structural modification relative to the Φ29 DNA polymerase selected from: a deletion of the NipTuck domain (residues 505-525), a deletion within the NipTuck domain, a K135A mutation, an E375H mutation, an E375S mutation, an E375K muatation, an E375R muatation, an E375A mutation, an E375Q mutation, an E375W mutation, an E375Y mutation, an E375F mutation, an L384R mutation, an E486A mutation, an E486D mutation, a K512A mutation, an N62D mutation, a D12A mutation, a T15I mutation, an E141 mutation, a D66A mutation, and/or combinations thereof.

Any of a variety of artificial surface coupling domains are included within the scope of the invention. The artificial surface coupling domain can simply be an in-frame fusion of a recombinant sequence to the enzyme, or it can be added post-translationally to the enzyme, e.g., chemically. Example coupling domains include any of: an added recombinant dimer domain of the enzyme, a large extraneous polypeptide domain, a polyhistidine tag, a HIS-6 tag, a His-10 tag, a biotin, an avidin sequence, a GST sequence, a glutathione, a BiTag (AviTag) sequence, an S tag, a SNAP-tag, an antibody, an antibody domain, an antibody fragment, an antigen, a receptor, a receptor domain, a receptor fragment, a ligand, a dye, an acceptor, a quencher, an oligonucleotide linker, and/or a combination thereof. The artificial surface coupling domains can include purification tags which are used, e.g., for polymerase purification, e.g., prior to binding of the polymerase to the surface (optionally through these same purification tags, or, optionally through different or additional surface binding domains).

In one aspect, the coupling domain is relatively large, e.g., at least 5 kDa in size. The relatively large size of the domain insulates the active site of the polymerase from surface effects, e.g., helping to prevent denaturation of the polymerase on the surface. The surface coupling domain can be e.g., at least 10 kDa, at least 20 kDa, at least 50 kDa, at least 100 kDa, or at least 1000 kDa or larger in size. These large coupling domains can include any of those listed herein and optionally can include one or more additional sequences. For example, the domains can include a poly-His sequence fused to a large extraneous polypeptide sequence that is fused in frame to the polymerase sequence. The large coupling domain can also include two or more separate surface coupling elements, e.g., a poly-His sequence and a GST sequence.

In various embodiments, 1, 2, 3, 4, 5 . . . 10 or more coupling domains (which are optionally the same, or are optionally different domains) can be included in the polymerase (each of which can have 1, 2, 3 . . . or more different surface coupling elements). For example, in one specific embodiment, at least two different artificial coupling domains that are specifically bound by at least two different cognate binding components are included. In another example, at least three different artificial coupling domains that are specifically bound by at least three different cognate binding components are included.

Preferably, the artificial surface coupling domains are distal to an active site of the polymerase. This acts to orient the polymerase active site away from the surface, making it accessible to ligands of the polymerase, and avoiding surface effects on the active site region of the polymerase. For example, when the active site is located within a C-terminal domain of the enzyme (e.g., as in phi 29 polymerases), the artificial surface coupling domain is located within an N-terminal domain of the enzyme. Polymerase orientation can be fixed relative to the surface through the use of multiple surface binding domains, by inhibiting polymerase rotation around surface coupling bonds. The use of multiple surface domains also increases binding affinity of the polymerase for a surface; for example, two surface coupling domains can have a higher binding affinity than binding of the polymerase to the surface through a single surface coupling domain (e.g., where the surface coupling domains have approximately additive effects on the overall binding affinity of the polymerase for the surface). The use of multiple domains can also facilitate purification and/or control release of the polymerase from a surface, by providing multiple different release mechanisms (e.g., coordinating metals from a nickel NTA binding domain in a first step, followed by other different release mechanisms such as heat, light, salt concentration, acid, base, etc., in a second controlled release step, depending on the nature of the additional coupling domains).

An advantage of the present system is that relatively high activity can be retained for the polymerase when bound to a surface. For example, the polymerase will typically have a $k_{cat}/K_m$ (or $V_{max}/K_m$) that is at least about 1%, at least about 10%, at least about 25%, at least about 50% or at least about 75% as high as the enzyme in solution, or higher.

Accordingly, in a related aspect, the invention provides a surface comprising an active polymerase bound thereon. The polymerase is coupled to the surface through a plurality of artificial or recombinant surface coupling domains as discussed above, and typically displays a $k_{cat}/K_m$ (or $V_{max}/K_m$) that is at least about 1%, at least about 10%, at least about 25%, at least about 50%, or at least about 75% as high as a corresponding active polymerase in solution.

Optionally, a location of the polymerase on the surface is fixed, thereby providing a spatial address of the polymerase on the surface. The surface itself can be a planar surface, such as a chip, plate, slide, or the like, or can be a curved surface, e.g., as in a microwell plate, or can be a bead or other regular or irregular surface. The surface can include a polymer, a ceramic, glass, a bead, a micro- or nano-bead, a polymer bead, a glass bead, a well, a micro- or nano-well, a slide, a grid, a rotor, a microchannel, or the like. The surface can be part of any existing instrumentation, e.g., in just one example, the surface can include or be proximal to a Zero Mode Wave guide, which is used, e.g., for various sequencing applications that benefit from an active surface-bound DNA polymerase.

Methods of amplifying or partially amplifying a DNA template are provided, e.g., for sequencing and/or amplification applications. The methods include, e.g., contacting a surface immobilized DNA polymerase with a template and amplification reagents under conditions that permit amplification of the template by the DNA polymerase, and permitting the DNA polymerase to amplify or partially amplify the template. All of the features discussed above for the polymerase, the surface, etc., are applicable to these methods. The polymerase can be pre-bound to the surface, or can be bound to the surface during amplification.

The methods can include features suitable to the application. For example, the template can include a circular DNA, e.g., where the application for the surface bound polymerase is rolling circle replication (or, e.g., certain sequencing applications where circular templates are useful). Alternately, where replication of a linear template is desirable, a linear template is used. Replication reagents can include any of a variety of reagents, including buffers, salts, nucleotides, and the like. In one embodiment, nucleotide analogues are used for applications in which incorporation of analogues, e.g., for various sequencing or labeling methods, is desired. In one example, the amplification reagents include one or more phosphate, sugar or base labeled nucleotide analog(s).

Permitting the DNA polymerase to amplify or partially amplify the template can include isothermal incubation of the DNA polymerase, the amplification reagents and the template, e.g., where the application is an isothermal amplification or sequencing reaction. Alternately, a thermocyclic incubation of the DNA polymerase, the amplification reagents and the template can be performed, as in PCR or various thermal-cycled sequencing methods. In one particular aspect, the reagents can be contacted to the polymerase proximal to a Zero Mode Waveguide, e.g., as in various sequencing methods that benefit from use of an immobilized DNA polymerase in a very small fluid volume proximal to such waveguides.

The methods can include selecting an addressable site for binding of the polymerase to the surface and binding the polymerase to the addressable site. This provides a fixed location for a particular sequencing or amplification reaction, which can then be monitored.

Methods of attaching an active DNA polymerase to a surface are also provided. The methods include: (a) providing a surface-coupleable DNA polymerase that comprises a surface coupling domain distal to an active site of the DNA polymerase; and (b) contacting the surface-coupleable DNA polymerase to the substrate. The coupling domain couples to the surface to provide the resulting surface immobilized active DNA polymerase. The surface coupling domain is artificial or recombinant, e.g., any of those as discussed above.

The surface coupling domain is optionally activatable, e.g., photocaged. This facilitates controlled coupling to the surface. Contacting the polymerase to the surface can include activating (e.g., uncaging) the surface coupling domain. This activation can include, e.g., proteolysis, photolysis, chemical treatment of the polymerase or binding of an intermediate coupling moiety to the substrate.

DETAILED DESCRIPTION

Overview

Figure 1:
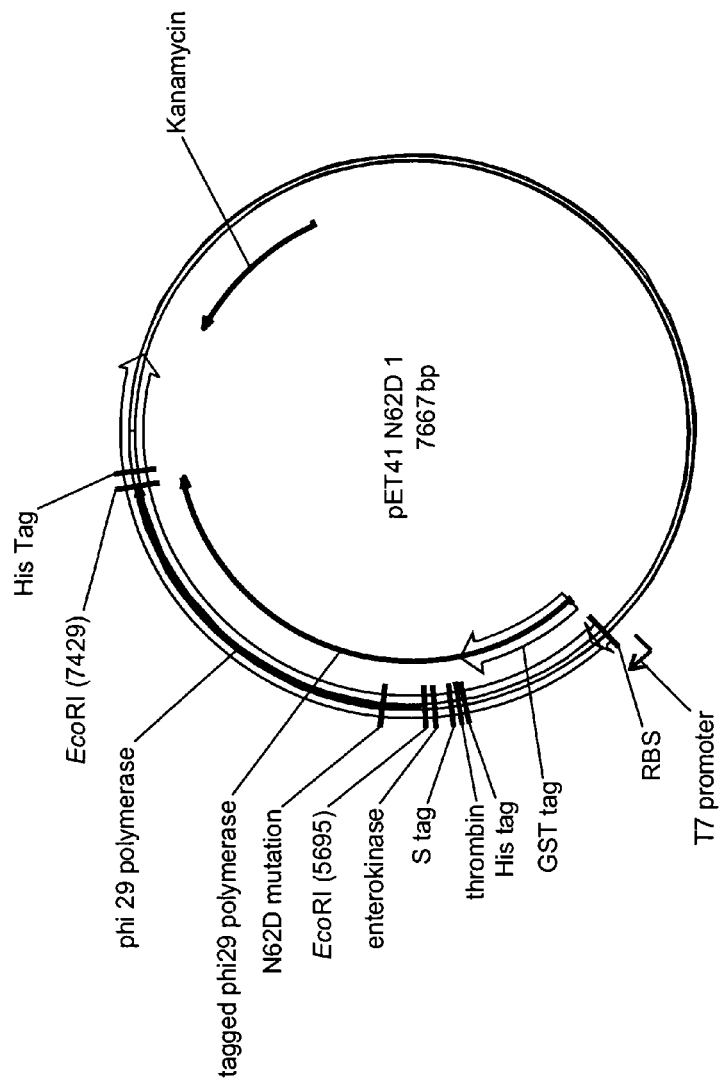
FIG. 1 schematically depicts a vector for expression of a recombinant Phi 29 DNA polymerase having three surface coupling domains.

The ability to couple DNA polymerases to surfaces is useful in a variety of settings. For example, any polymerase activity can be measured in a solid phase format by binding the polymerase to a surface and performing the relevant assay. The ability to bind the polymerase to the surface has several advantages, including, but not limited to: the ability to purify, capture and assess polymerase reactions using a single substrate; the ability to re-use the polymerase by washing template and reagents off of the solid phase between uses; the ability to format bound polymerases into a spatially defined set of reactions by selecting where the polymerase is bound onto the solid phase, facilitating monitoring of the reactions (e.g., using available array detectors); the ability to perform and detect single-molecule reactions at defined sites on the substrate (thereby reducing reagent consumption); the ability to monitor multiple different polymerases on a single surface to provide a simple readout of multiple polymerase reactions at once, e.g., in biosensor applications; and many others.

There are several problems in the prior art associated with coupling polymerases to surfaces. These include protein denaturation on the surface (e.g., due to hydrophobic or hydrophilic properties of the surface, or even simply steric effects between the protein and the surface); a lack of specific orientation of bound polymerases, providing inconsistent properties between bound polymerases, depending on orientation of the polymerase relative to the substrate; a lack of sufficient affinity between the polymerase and the surface; a lack of controllability of binding of the polymerase to a surface, and others.

The present invention overcomes these difficulties by various interrelated approaches. First, to combat surface effects, the polymerase can be coupled to a relatively large insulating linker moiety such as a large protein domain (at least 5 kDa, and preferably larger) that insulates the polymerase from the surface. Second, two or more surface binding elements can be used to specifically orient the polymerase relative to the surface (binding of the overall protein to the surface at two or more sites inhibits rotation of the polymerase and tends to orient the polymerase relative to the surface). Third, the insulating moiety and/or the surface binding elements are placed distal to the biologically relevant portion of the protein, e.g., the active site.

Accordingly, an advantageous feature of the invention is that polymerase can be coupled to a surface using large insulating domains and/or multiple coupling sites to the surface, without substantial loss of polymerase activity. Single molecule polymerase readouts (or small number of molecule readouts) can be achieved, with reasonable consistency between individual surface-bound polymerase molecules, facilitating a variety of extremely small volume reactions.

Accordingly, isolated and/or recombinant polymerases comprising surface binding domains, surfaces with active polymerase bound to them, and methods of coupling polymerase to surfaces are all features of the invention. Methods of amplifying nucleic acids (e.g., DNA templates) using a polymerase bound to a surface are also features of the invention.

DNA Polymerases

DNA polymerases as used herein are enzymes that produce DNA polymers. DNA polymerases that can be modified to include surface binding domains are generally available. For example, DNA template-dependent DNA polymerases have relatively recently been classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" *J Biol. Chem.* 276(47):43487-90. For a review of polymerases, see, e.g., Hübscher et al. (2002) EUKARYOTIC DNA POLYMERASES *Annual Review of Biochemistry* Vol. 71: 133-163; Alba (2001) "Protein Family Review: Replicative DNA Polymerases" *Genome Biology* 2(1):reviews 3002.1-3002.4; and Steitz (1999) "DNA polymerases: structural diversity and common mechanisms" *J Biol Chem* 274:17395-17398. The basic mechanisms of action for many polymerases have been determined. The sequences of literally hundreds of polymerases are publicly available, and the crystal structures for many of these have been determined, or can be inferred based upon similarity to solved crystal structures for homologous polymerases.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. Any of these available polymerases can be modified in accordance with the invention to include surface binding domains. Many such polymerases that are suitable for modification are available, e.g., for use in sequencing, labeling and amplification technologies. For example, Human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Phi29 DNA polymerase is available from e.g., Epicenter. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase is available from New England Biolabs; GoTaq® Flexi DNA Polymerase available from Promega; RepliPHI™ Phi29 DNA Polymerase from EPICENTRE; PfuUltra™ Hotstart DNA Polymerase available from Stratagene; KOD HiFi DNA Polymerase is available from Novagen and many others. Telomerase is available from one or more sources. Biocompare(dot)com provides comparisons of many different commercially available polymerases.

DNA polymerases that are preferred substrates for modification to include surface binding domains include Taq polymerases, exonuclease deficient Taq polymerases, E. coli DNA Polymerase 1, Klenow fragment, reverse transcriptases, Φ29 related polymerases including wild type Φ29 polymerase and derivatives of such polymerases such as exonuclease deficient forms, T7 DNA Polymerase, T5 DNA Polymerase, etc. For example, the recombinant DNA polymerase can be homologous to a wild-type or exonuclease deficient Phi 29 DNA polymerase, e.g., as described in U.S. Pat. No. 5,001,050, 5,198,543, or 5,576,204, the full disclosures of which are incorporated herein by reference in their entirety for all purposes. Similarly, the recombinant DNA polymerase can be homologous to Φ29, B103, GA-1, PZA, Φ15, BS32, M2Y, Nf, G1, Cp-1, PRD1, PZE, SFS, Cp-5, Cp-7, PR4, PR5, PR722, L17 and/or the like.

The recombinant DNA polymerase optionally includes additional features exogenous or heterologous to the polymerase. For example, the recombinant polymerase optionally includes one or more exogenous affinity tags, e.g., purification or surface coupling domains, such as a 6 His tag sequence, a GST tag sequence, a plurality of 6 His tag sequences, a plurality of GST tag sequences, a SNAP-tag, or the like. These and other features useful in the context of binding a polymerase to a surface (and/or purifying the polymerase) are optionally included, e.g., to orient and/or protect the polymerase active site when the polymerase is bound to a surface. Other useful features include recombinant additional domains of the polymerase enzyme, and, e.g., large extraneous polypeptide domains coupled to the polymerase distal to the active site. For example, for Phi 29, it was determined that the active site is in the C terminal region of the protein. Therefore, it was determined that added surface binding elements (extra domains, His tags, etc.) are best located in the N-terminal region to avoid interfering with the active site when the polymerase is coupled to a surface.

Coupling Domains

An artificial surface coupling domain is a moiety that is heterologous to the polymerase of interest, and that is capable of binding to a binding partner that is coupled or bound to (and/or integral with) a surface. For convenience, the coupling domain will often be expressed as a fusion domain of the overall polymerase protein, e.g., as a conventional in-frame fusion of a polypeptide sequence with the active polymerase enzyme (e.g., a poly-His tag fused in frame to an active polymerase enzyme sequence). However, coupling domains can also be added chemically to the polymerase, e.g., by using an available amino acid residue of the enzyme, or by incorporating an amino acid into the protein that provides a suitable attachment site for the coupling domain. Suitable residues of the enzyme can include, e.g., histidine, cysteine or serine residues (providing for N, S or O linked coupling reactions), or glycosylation sites (e.g., the binding partner can be an antibody or receptor that binds to a polysaccharide glycosylation structure). Unnatural amino acids that comprise unique reactive sites can also be added to the enzyme, e.g., by expressing the enzyme in a system that comprises an orthogonal tRNA and an orthogonal synthetase that loads the unnatural amino acid in response to a selector codon.

A single type of coupling domain, or more than one type can be included. 1, 2, 3, 4, 5 . . . 10 or more coupling domains (which are optionally the same, or are optionally different domains) can be included in the polymerase enzyme. Furthermore each domain can have 1, 2, 3, 4, 5 . . . 10 or more different surface coupling elements. For example, a large surface coupling domain optionally includes multiple surface coupling elements. Alternatively, a small coupling domain such as a poly-His domain optionally includes a single coupling element (the poly-His sequence).

As noted previously, the coupling domains are advantageously placed distal to the active site of the polymerase to avoid affecting polymerase activity.

Figure 2:
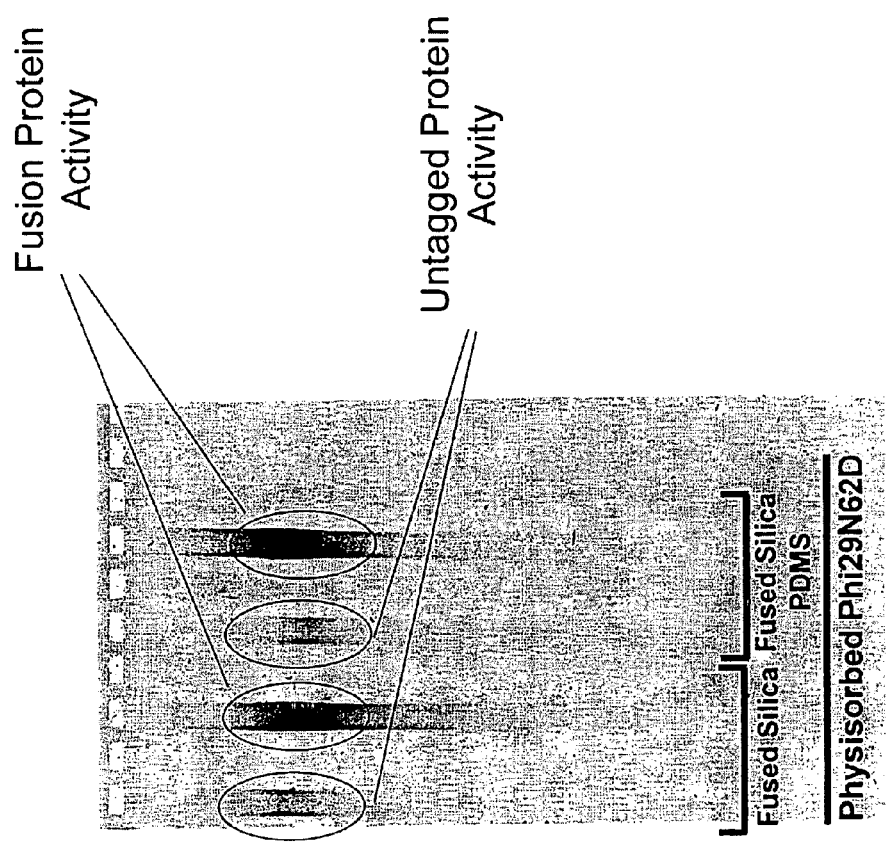
FIG. 2 schematically shows results of an experiment in which polymerases tethered to a fused silica surface (both with and without a PDMS surface coating layer) via a GST linkage as described herein showed 8× greater activity than a similar polymerase that lacked the GST tag. This increase in activity is illustrated in the gel of nucleic acid synthesis products as shown.

As noted above, one advantage of the present system is that relatively high activity can be retained for the polymerase when bound to a surface. For example, results of an experiment with a polymerase (N62D Φ29) tethered to a fused silica surface (both with and without a PDMS surface coating layer) via a GST linkage as described herein showed 8× greater activity than a similar surface-bound polymerase that lacked the GST tag. This increase in activity is illustrated in the gel of nucleic acid synthesis products shown in FIG. 2.

Types of Coupling Domains/Elements

Example coupling domains (which can be coupled to the polymerase, e.g., as an in frame fusion domain or as a chemically coupled domain) include any of: an added recombinant dimer domain of the enzyme, a large extraneous polypeptide domain, a polyhistidine tag, a HIS-6 tag, a biotin, an avidin sequence, a GST sequence, a glutathione, a BiTag (AviTag) sequence, an S tag, a SNAP-tag, an antibody, an antibody domain, an antibody fragment, an antigen, a receptor, a receptor domain, a receptor fragment, a ligand, a dye, an acceptor, a quencher, and/or a combination thereof. The artificial surface coupling domains can include purification tags which are used, e.g., for polymerase enzyme purification, e.g., prior to binding of the enzyme to the surface (optionally through these same purification tags, or, optionally through different or additional surface binding domains), or concomitant with binding to the surface (e.g., the surface is optionally used for affinity capture of the polymerase).

A large number of tags are known in the art and can be adapted to the practice of the present invention by being incorporated as coupling domains/elements. For example, see, e.g.: Nilsson et al. (1997) "Affinity fusion strategies for detection, purification, and immobilization of recombinant proteins" Protein Expression and Purification 11: 1-16, Terpe et al. (2003) "Overview of tag protein fusions: From molecular and biochemical fundamentals to commercial systems" Applied Microbiology and Biotechnology 60:523-533, and references therein). Tags that can be used to couple the polymerase to the surface through binding to an immobilized binding partner include, but are not limited to, a polyhistidine tag (e.g., a His-6, His-8, or His-10 tag) that binds immobilized divalent cations (e.g., $Ni^{2+}$), a biotin moiety (e.g., on an in vivo biotinylated polypeptide sequence) that binds immobilized avidin, a GST (glutathione S-transferase) sequence that binds immobilized glutathione, an S tag that binds immobilized S protein, an antigen that binds an immobilized antibody or domain or fragment thereof (including, e.g., T7, myc, FLAG, and B tags that bind corresponding antibodies), a FLASH Tag (a high affinity tag that couples to specific arsenic based moieties), a receptor or receptor domain that binds an immobilized ligand (or vice versa), protein A or a derivative thereof (e.g., Z) that binds immobilized IgG, maltose-binding protein (MBP) that binds immobilized amylose, an albumin-binding protein that binds immobilized albumin, a chitin binding domain that binds immobilized chitin, a calmodulin binding peptide that binds immobilized calmodulin, and a cellulose binding domain that binds immobilized cellulose. Another exemplary tag that can be used to couple the enzyme to the surface is a SNAP-tag, commercially available from Covalys (www(dot)covalys(dot)com). The SNAP-tag is an approximately 20 kDa version of a protein $O^6$-alkylguanine-DNA alkyltransferase which has a single reactive cysteine with a very high affinity for guanines alkylated at the $O^6$-position. The alkyl group, including any immobilization moiety attached to the alkyl group (e.g., a surface-immobilized alkyl group), is transferred covalently from the guanine to the cysteine in the alkyltransferase protein.

One or more specific protease recognition sites are optionally included in a coupling domain, for example, between adjacent tags or between a tag and the polymerase. Example specific proteases include, but are not limited to, thrombin, enterokinase, factor Xa, TEV protease, and HRV 3C protease. Similarly, an intein sequence can be incorporated into a coupling domain (e.g., an intein that undergoes specific self cleavage in the presence of free thiols). Such protease cleavage sites and/or inteins are optionally used to remove a tag used for purification of the polymerase enzyme and/or for releasing the enzyme from the surface.

Large Coupling Domains

In one aspect, the coupling domain is relatively large, e.g., at least 5 kDa in size. These large domains can be added to the protein recombinantly (e.g., as in-frame fusions) or post-translationally (e.g., chemically). The relatively large size of the domain insulates the active site of the polymerase from surface effects, e.g., helping to prevent denaturation of the polymerase on the surface (here again, the large domain is typically coupled to the polymerase distal to an active site of the polymerase). The surface coupling domain can be e.g., at least 5 kDa, at least 10 kDa, at least 20 kDa, at least 50 kDa, at least 100 kDa, at least 1000 kDa or larger in size. These large coupling domains can include any of those listed herein and optionally can include one or more additional sequences. For example, the domains can include a poly-His sequence fused to a large extraneous surface insulating polypeptide sequence that is fused in frame to the enzyme sequence. The large coupling domain can also include two or more separate surface coupling elements, e.g., a poly-His sequence and a GST sequence.

Examples of large coupling domains can include, e.g., one or more polypeptide sequence. For example, a sequence that is inactive relative to the polymerase of interest (e.g., has little or no effect on polymerase activity) can be used. Such sequences include polypeptide chains of known polypeptides, random sequences, or sequences selected by the user. Sequences that are likely to disrupt folding of the polymerase are typically avoided, e.g., the large coupling domain is typically selected to avoid charged or reactive residues proximal to the active enzymatic domains of a fusion polymerase protein (though the large domain can present charged or reactive residues distal to the enzyme, e.g., to interact with the surface or binding partner). Large coupling domains can include synthetically generated polypeptide sequences, or they can optionally comprise portions or all of complete proteins that do not otherwise substantially interfere in the activity of the polymerase enzyme. In some cases, for example, the binding domain optionally comprises a polymerase dimer molecule, e.g., a fusion of two polymerase molecules, where one operates as the surface binding domain.

The large coupling domain can fold upon translation into a defined structure, e.g., as a protein or protein domain. A wide variety of structurally discrete domains are known in the literature and can be used as large coupling domains. The NCBI, GeneBank and others provide extensive lists of known polypeptide sequences that can be used, in whole or in part, as large coupling domains. Furthermore, random sequences, or sequences designed by the user to have appropriate properties (e.g., by including coupling elements, charged features proximal to oppositely charged surface features, regions of secondary structure such as helixes, turns, hydrophobic or hydrophilic domains, etc.) can be used. These structures can be partially or fully denatured upon binding to the surface, insulating or "cushioning" the active enzyme from the surface.

Fusion Proteins

The recombinant construction of fusion proteins is generally well known and can be applied to the present invention to incorporate coupling domains or elements. In brief, a nucleic acid that encodes the coupling domain or element is fused in frame to a nucleic acid encoding the polymerase of interest. The resulting fusion nucleic acid is expressed (in vitro or in vivo) and the expressed fusion protein is isolated, e.g., by standard methods and/or by binding coupling elements, e.g., comprising purification tags, to surfaces. Coupling domains or elements are typically fused N-terminal and/or C-terminal to the enzyme, but are optionally internal to the enzyme (e.g., incorporated into a surface loop or the like) where such incorporation does not interfere with function of the enzyme or domain).

References that discuss recombinant methods that can be used to construct fusion nucleic acids and to create fusion proteins include Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2005) ("Ausubel")) and *PCR Protocols A Guide to Methods and Applications* (Innis et al. eds) Academic Press Inc. San Diego, Calif. (1990) (Innis).

In addition, a plethora of kits are commercially available for cloning, recombinant expression and purification of plasmids or other relevant nucleic acids from cells, (see, e.g., EasyPrep™, FlexiPrep™, both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both. See, Giliman & Smith, *Gene* 8:81 (1979); Roberts, et al., *Nature,* 328:731 (1987); Schneider, B., et al., *Protein Expr. Purif.* 6435:10 (1995); Ausubel, Sambrook, Berger (above). A catalogue of Bacteria and Bacteriophages useful for cloning is provided, e.g., by the ATCC, e.g., *The ATCC Catalogue of Bacteria and Bacteriophage* published yearly by the ATCC. Additional basic procedures for sequencing, cloning and other aspects of molecular biology and underlying theoretical considerations are also found in Watson et al. (1992) Recombinant DNA Second Edition, Scientific American Books, NY.

Other useful references, e.g. for cell isolation and culture (e.g., for subsequent nucleic acid isolation and fusion protein expression) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture;* Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

In addition, essentially any fusion nucleic acid can be custom or standard ordered from any of a variety of commercial sources, such as Operon Technologies Inc. (Alameda, Calif.).

A variety of protein isolation and detection methods are known and can be used to isolate polymerases, e.g., from recombinant cultures of cells expressing fusion protein enzymes of the invention. A variety of protein isolation and detection methods are well known in the art, including, e.g., those set forth in R. Scopes, *Protein Purification*, Springer-Verlag, N.Y. (1982); Deutscher, *Methods in Enzymology* Vol. 182: Guide to Protein Purification, Academic Press, Inc. N.Y. (1990); Sandana (1997) *Bioseparation of Proteins*, Academic Press, Inc.; Bollag et al. (1996) *Protein Methods, 2$^{nd}$ Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3$^{rd}$ Edition* Springer Verlag, NY; Janson and Ryden (1998) *Protein Purification: Principles, High Resolution Methods and Applications, Second Edition* Wiley-VCH, NY; Walker (2002) *Protein Protocols on CD-ROM,* version 2.0 Humana Press, NJ; *Current Protocols in Protein Science,* John E. Coligan et al., eds., Current Protocols, a joint venture between Greene Publishing Associates, Inc. and John Wiley & Sons, Inc., (supplemented through 2005); and the references cited therein. Additional details regarding protein purification and detection methods can be found in Satinder Ahuja ed., *Handbook of Bioseparations,* Academic Press (2000).

Adding Coupling Domains Chemically

In addition to the convenient recombinant expression of fusion proteins comprising coupling domains, the coupling domains can also alternatively or additionally be coupled to the enzyme chemically. For example, N, S or O containing residues of the polymerase (or added recombinantly to the polymerase) can be coupled through standard chemical methods to coupling domains that comprise groups that bind these residues.

In addition, systems of orthogonal components are available that can incorporate any of a variety of chemically reactive unnatural amino acids into a recombinant protein (e.g., polymerase of the invention). In brief, a cell or other translation system is constructed that includes an orthogonal tRNA ("OtRNA"; a tRNA not recognized by the cell's endogenous translation machinery, such as an amber or 4-base tRNA) and an orthogonal tRNA synthetase ("ORS"; this is a synthetase that does not aminoacylate any endogenous tRNA of the cell, but which can aminoacylate the OtRNA in response to a selector codon). A nucleic acid encoding the enzyme is constructed to include a selector codon at a selected that is specifically recognized by the OtRNA. The ORS specifically incorporates an unnatural amino acid with a desired chemical functionality at one or more selected site(s) (e.g., distal to the active site). This chemical functional group can be unique as compared to those ordinarily found on amino acids, e.g., that incorporate keto or other functionalities. These are coupled to the coupling domains through appropriate chemical linkages.

Further information on orthogonal systems can be found, e.g., in Wang et al., (2001), *Science* 292:498-500; Chin et al., (2002) *Journal of the American Chemical Society* 124:9026-9027; Chin and Schultz, (2002), *ChemBioChem* 11:1135-1137; Chin, et al., (2002), *PNAS United States of America* 99:11020-11024; and Wang and Schultz, (2002), *Chem. Comm.,* 1-10. See also, International Publications WO 2002/086075, entitled "METHODS AND COMPOSITIONS FOR THE PRODUCTION OF ORTHOGONAL tRNA AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; and WO 2005/007624, filed Jul. 7, 2004.

Orientation Properties

Preferably, the artificial surface coupling domains are distal to an active site of the polymerase enzyme. This acts to orient the polymerase's active site away from the surface, making it accessible to polymerase substrates (template, nucleotides, etc.), and avoiding surface effects on the active site region of the enzyme. For example, when the active site is located within a C-terminal domain of the polymerase (e.g., as in Φ29 polymerases), the artificial surface coupling domain is located within an N-terminal domain of the enzyme. Polymerase orientation can be fixed relative to the surface through the use of multiple surface binding domains, by inhibiting polymerase rotation around surface coupling bonds. The use of multiple surface domains also increases binding affinity of the polymerase for a surface; for example, two surface coupling domains can have a higher binding affinity than binding of the polymerase to the surface through a single surface coupling domain (e.g., where the surface coupling domains have additive or synergistic effects on the overall binding affinity of the polymerase for the surface). The use of multiple domains can also facilitate purification and/or control release of the polymerase from a surface, by providing multiple different release mechanisms (e.g., coordinating metals from a nickel NTA binding domain in a first step, followed by other different release mechanisms such as heat, light, salt concentration, acid, base, site-specific protease treatment, binding competition, etc., in a second controlled release step, depending on the nature of the additional coupling domains).

Controllable Coupling

In many solid-phase applications, it is useful to control coupling of the surface coupling domain and the binding partner. For example, standard chip masking strategies can be used to selectively block or expose surface bound binding partners to one or more un-blocking action (exposure to light, heat, chemicals, pH, protein blocking agents, etc.). The coupling domain can similarly be blocked until it is desirable to couple it to the binding partner. This blocking/unblocking approach can be used to create complex arrays of polymerases coupled to the surface. This is useful in array-based applications, e.g., where the activity of the polymerase is monitored at selected sites on the array, e.g., using array detectors such as diode array detectors, CCDs, ICCDs or EMCCDs.

Thus, coupling of the surface coupling domain to the surface is optionally controlled by caging the surface coupling domain and/or its binding partner. The surface coupling domain or its partner can be caged, for example, by attachment of at least one photolabile caging group to the domain or partner; the presence of the caging group prevents the interaction of the surface coupling domain with its binding partner, while removal of the caging group by exposure to light of an appropriate wavelength permits the interaction to occur. The photolabile caging group can be, e.g., a relatively small moiety such as carboxyl nitrobenzyl, 2-nitrobenzyl, nitroindoline, hydroxyphenacyl, DMNPE, or the like, or it can be, e.g., a relatively bulky group (e.g. a macromolecule, a protein) covalently attached to the molecule by a photolabile linker (e.g., a polypeptide linker comprising a 2-nitrophenyl glycine residue). Other caging groups can be removed from a molecule, or their interference with the molecule's activity can be otherwise reversed or reduced, by exposure to an appropriate type of uncaging energy and/or exposure to an uncaging chemical, enzyme, or the like.

A large number of caging groups, and a number of reactive compounds that can be used to covalently attach caging groups to other molecules, are well known in the art. Examples of photolabile caging groups include, but are not limited to: nitroindolines; N-acyl-7-nitroindolines; phenacyls; hydroxyphenacyl; brominated 7-hydroxycoumarin-4-ylmethyls (e.g., Bhc); benzoin esters; dimethoxybenzoin; meta-phenols; 2-nitrobenzyl; 1-(4,5-dimethoxy-2-nitrophenyl)ethyl (DMNPE); 4,5-dimethoxy-2-nitrobenzyl (DMNB); alpha-carboxy-2-nitrobenzyl (CNB); 1-(2-nitrophenyl)ethyl (NPE); 5-carboxymethoxy-2-nitrobenzyl (CMNB); (5-carboxymethoxy-2-nitrobenzyl)oxy) carbonyl; (4,5-dimethoxy-2-nitrobenzyl)oxy) carbonyl; desoxybenzoinyl; and the like. See, e.g., U.S. Pat. No. 5,635,608 to Haugland and Gee (Jun. 3, 1997) entitled "α-carboxy caged compounds"; *Neuro* 19, 465 (1997); *J Physiol* 508.3, 801 (1998); *Proc Natl Acad Sci USA* 1988 September, 85(17): 6571-5; *J Biol Chem* 1997 Feb. 14, 272(7):4172-8; *Neuron* 20, 619-624, 1998; *Nature Genetics*, vol. 28:2001:317-325; *Nature*, vol. 392, 1998:936-941; Pan, P., and Bayley, H. "Caged cysteine and thiophosphoryl peptides" *FEBS Letters* 405:81-85 (1997); Pettit et al. (1997) "Chemical two-photon uncaging: a novel approach to mapping glutamate receptors" *Neuron* 19:465-471; Furuta et al. (1999) "Brominated 7-hydroxycoumarin-4-ylmethyls: novel photolabile protecting groups with biologically useful cross-sections for two photon photolysis" *Proc. Natl. Acad. Sci.* 96(4):1193-1200; Zou et al. "Catalytic subunit of protein kinase A caged at the activating phosphothreonine" *J. Amer. Chem. Soc.* (2002) 124:8220-8229; Zou et al. "Caged Thiophosphotyrosine Peptides" *Angew. Chem. Int. Ed.* (2001) 40:3049-3051; Conrad II et al. "p-Hydroxyphenacyl Phototriggers The reactive Excited State of Phosphate Photorelease" *J. Am. Chem. Soc.* (2000) 122:9346-9347; Conrad II et al. "New Phototriggers 10: Extending the π,π* Absorption to Release Peptides in Biological Media" *Org. Lett.* (2000) 2:1545-1547; Givens et al. "A New Phototriggers 9: p-Hydroxyphenacyl as a C-Terminus Photoremovable Protecting Group for Oligopeptides" *J. Am. Chem. Soc.* (2000) 122:2687-2697; Bishop et al. "40-Aminomethyl-2,20-bipyridyl-4-carboxylic Acid (Abc) and Related Derivatives: Novel Bipyridine Amino Acids for the Solid-Phase Incorporation of a Metal Coordination Site Within a Peptide Backbone" *Tetrahedron* (2000) 56:4629-4638; Ching et al. "Polymers As Surface-Based Tethers with Photolytic triggers. Enabling Laser-Induced Release/Desorption of Covalently Bound Molecules" Bioconjugate *Chemistry* (1996) 7:525-8; *BioProbes Handbook,* 2002 from Molecular Probes, Inc.; and *Handbook of Fluorescent Probes and Research Products*, Ninth Edition or Web Edition, from Molecular Probes, Inc, as well as the references below.

Caged polymerases (e.g., caged surface coupling domains and/or binding partners) can be produced, e.g., by reacting a polypeptide with a caging compound or by incorporating a caged amino acid during synthesis of a polypeptide. See, e.g., U.S. Pat. No. 5,998,580 to Fay et al. (Dec. 7, 1999) entitled "Photosensitive caged macromolecules"; Kossel et al. (2001) *PNAS* 98:14702-14707; *Trends Plant Sci* (1999) 4:330-334; *PNAS* (1998) 95:1568-1573; *J Am Chem Soc* (2002) 124: 8220-8229; *Pharmacology & Therapeutics* (2001) 91:85-92; and *Angew Chem Int Ed Engl* (2001) 40:3049-3051. A polypeptide can be reacted with a caged biotin (see, e.g., Pirrung and Huang (1996) "A general method for the spatially defined immobilization of biomolecules on glass surfaces using 'caged' biotin" *Bioconjug Chem*. 7:317-21). As another example, a photolabile polypeptide linker (e.g., comprising a photolabile amino acid such as that described in U.S. Pat. No. 5,998,580, supra) can be used to link a bulky caging group (e.g., another polypeptide that blocks the interaction between the surface coupling domain and its binding partner) to the surface coupling domain or partner.

Useful site(s) of attachment of caging groups to a given molecule can be determined by techniques known in the art. For example, a surface coupling domain can be reacted with a caging compound. The resulting caged surface coupling domain can then be tested to determine if its interaction with its binding partner is sufficiently blocked. As another example, for a polypeptide surface coupling domain, amino acid residues located at the surface coupling domain-partner binding interface can be identified by routine techniques such as scanning mutagenesis, sequence comparisons and site-directed mutagenesis, or the like. Such residues in the coupling domain can then be caged, and the activity of the caged surface coupling domain can be assayed to determine the efficacy of caging.

Appropriate methods for uncaging caged molecules are also known in the art. For example, appropriate wavelengths of light for removing many photolabile groups have been described; e.g., 300-360 nm for 2-nitrobenzyl, 350 nm for benzoin esters, and 740 nm for brominated 7-hydroxycoumarin-4-ylmethyls (see, e.g., references herein). Conditions for uncaging any caged molecule (e.g., the optimal wavelength for removing a photolabile caging group) can be determined according to methods well known in the art. Instrumentation and devices for delivering uncaging light are likewise known; for example, well-known and useful light sources include e.g., a lamp or a laser.

Properties of Bound Enzymes/Determining Kinetic Parameters

The bound polymerase will typically have a $k_{cat}/K_m$ (or $V_{max}/K_m$) that is at least 10% as high as the polymerase in solution. Often the level will be at least 50% as high as the polymerase in solution, or 75% as high as the polymerase in solution, 90% as high as the polymerase in solution, or higher.

The polymerase enzymes of the invention can be screened (in solution or on a solid phase) or otherwise tested to determine whether and to what degree the enzyme is active. For example, $k_{cat}$, $K_m$, $V_{max}$, or $k_{cat}/K_m$ of the enzyme can be determined.

For example, as is well-known in the art, for enzymes obeying simple Michaelis-Menten kinetics, kinetic parameters are readily derived from rates of catalysis measured at different substrate concentrations. The Michaelis-Menten equation, $V=V_{max}[S]([S]-K_m)^{-1}$, relates the concentration of uncombined substrate ([S], approximated by the total substrate concentration), the maximal rate ($V_{max}$, attained when the enzyme is saturated with substrate), and the Michaelis constant ($K_m$, equal to the substrate concentration at which the reaction rate is half of its maximal value), to the reaction rate (V).

For many polymerase enzymes, $K_m$ is equal to the dissociation constant of the enzyme-substrate complex and is thus a measure of the strength of the enzyme-substrate complex. For such an enzyme, in a comparison of $K_m$s, a lower $K_m$ represents a complex with stronger binding, while a higher $K_m$ represents a complex with weaker binding. The ratio $k_{cat}/K_m$, sometimes called the specificity constant, represents the apparent rate constant for combination of substrate with free enzyme. The larger the specificity constant, the more efficient the enzyme is in binding the substrate and converting it to product.

The $k_{cat}$ (also called the turnover number of the enzyme) can be determined if the total enzyme concentration ($[E_T]$, i.e., the concentration of active sites) is known, since $V_{max}=k_{cat}[E_T]$. For situations in which the total enzyme concentration is difficult to measure, the ratio $V_{max}/K_m$ is often used instead as a measure of efficiency. $K_m$ and $V_{max}$ can be determined, for example, from a Lineweaver-Burke plot of 1/V against 1/[S], where the y intercept represents $1/V_{max}$, the x intercept $-1/K_m$, and the slope $K_m/V_{max}$, or from an Eadie-Hofstee plot of V against V/[S], where the y intercept represents $V_{max}$, the x intercept $V_{max}/K_m$, and the slope $-K_m$. Software packages such as KinetAsyst™ or Enzfit (Biosoft, Cambridge, UK) can facilitate the determination of kinetic parameters from catalytic rate data.

For enzymes such as polymerases that have multiple substrates, varying the concentration of only one substrate while holding the others constant typically yields normal Michaelis-Menten kinetics.

For a more thorough discussion of enzyme kinetics, see, e.g., Berg, Tymoczko, and Stryer (2002) *Biochemistry, Fifth Edition*, W. H. Freeman; Creighton (1984) *Proteins: Structures and Molecular Principles*, W. H. Freeman; and Fersht (1985) *Enzyme Structure and Mechanism, Second Edition*, W. H. Freeman.

Amplification of DNA Templates by Immobilized Polymerases

A surface immobilized DNA polymerase of the invention can be used to amplify a DNA template. The immobilized polymerase is contacted with the template and amplification reagents under conditions that permit amplification of the template by the polymerase, and the polymerase is permitted to amplify or partially amplify the template.

A wide variety of techniques for amplifying nucleic acids are known in the art and can be adapted to the practice of the present invention. The template DNA can be a linear or circular DNA, and in certain applications, is desirably a circular template (e.g., for rolling circle amplification or for sequencing of circular templates). Typical amplification reagents include at least one primer (e.g., an oligonucleotide primer) that is extended by the polymerase in a template-dependent manner, and a mixture of nucleotides and/or nucleotide analog(s). An aqueous buffered salt solution, any appropriate cofactors, and the like are provided as appropriate for the selected technique.

Temperature can also be controlled as appropriate for the selected technique as is well known in the art. For example, the DNA polymerase can amplify or partially amplify the template during an isothermal incubation of the polymerase, template, and amplification reagents. As another example, the polymerase can amplify or partially amplify the template during a thermocyclic incubation of the polymerase, template, and amplification reagents; amplification can thus involve one or more PCR (polymerase chain reaction) cycles. In PCR, a pair of primers flanking the region of the template to be amplified is typically provided. Template-dependent extension of the primers is catalyzed by the immobilized DNA polymerase, in the presence of deoxyribonucleoside triphosphates and/or nucleotide analogs (e.g., for labeling and/or termination). The PCR process typically involves cycles of three steps: denaturation (e.g., of double-stranded template and/or extension product), annealing (e.g., of one or more primers to template), and extension (e.g., of one or more primers to form double-stranded extension products). The PCR process can instead, e.g., involve cycles of two steps: denaturation (e.g., of double-stranded template and/or extension product) and annealing/extension (e.g., of one or more primers to template and of one or more primers to form double-stranded extension products). The cycles can involve, for example, cycles of denaturation at temperatures greater than about 90° C., annealing at 50-75° C., and extension at 60-78° C. A thermostable enzyme such as *Thermus aquaticus* Taq DNA polymerase is thus preferred. PCR techniques have been extremely well described in both the patent and the scientific literature, and any of a variety of such techniques can be employed, including, e.g., asymmetric PCR, quantitative real-time PCR, and the like.

Product formation can be monitored, for example, after the amplification is stopped or is complete, or in real time (e.g., by monitoring incorporation of a labeled nucleotide, nucleotide analog, or primer into the product or by dye binding to the double-stranded product). Amplification and/or detection of product is optionally automated, in an automated DNA amplification and/or sequencing system As noted, the amplification reagents optionally include one or more nucleotide analogs, e.g., one or more dideoxy nucleotide analog whose incorporation terminates copying of the template by the polymerase or one or more sugar-, base- or phosphate-labeled nucleotide analogs. Incorporation of labeled nucleotide analogs by the immobilized polymerases of the invention are particularly useful in a variety of different nucleic acid analyses. For example, analog incorporation can be used to indicate the presence and composition of a growing nucleic acid strand, e.g., providing evidence of template amplification and/or sequence of the template. Signaling from the incorporation can be the result of detecting labeling groups that are liberated from the incorporated analog or can arise upon the incorporation reaction. For example, in the case of FRET labels where a bound label is quenched and a free label is not, release of a label group from the incorporated analog can give rise to a fluorescent signal.

In one example reaction of interest, a polymerase reaction can be isolated within an extremely small observation volume that effectively results in observation of individual polymerase molecules. As a result, the incorporation event provides observation of an incorporating nucleotide analog that is readily distinguishable from non-incorporated nucleotide analogs. In a preferred aspect, such small observation volumes are provided by contacting the amplification reagents to the immobilized polymerase within or proximal to an optical confinement, such as a Zero Mode Waveguide (ZMW). For a description of ZMWs and their application in single molecule analyses, and particularly nucleic acid sequencing, see, e.g., Levene et al. "Zero-mode waveguides for single-molecule analysis at high concentrations" *Science* 299:682-686 (2003), Published U.S. Patent Application No. 2003/0044781, and U.S. Pat. No. 6,917,726, each of which is incorporated herein by reference in its entirety for all purposes.

In general, a polymerase enzyme is complexed with the template strand in the presence of one or more nucleotides and/or one or more nucleotide analogs. For example, in certain embodiments, labeled analogs are present representing analogous compounds to each of the four natural nucleotides, A, T, G and C, e.g., in separate polymerase reactions, as in classical sequencing, or equally preferably, in a single reaction. When a particular base in the template strand is encountered by the polymerase during the polymerization reaction, it complexes with an available analog that is complementary to such nucleotide, and incorporates that analog into the nascent and growing nucleic acid strand. In one aspect, incorporation can result in a label being released, e.g., in polyphosphate analogs, cleaving between the $\alpha$ and $\beta$ phosphorus atoms in the analog, and consequently releasing the labeling group (or a portion thereof). The incorporation event is detected, either by virtue of a longer presence of the analog, and thus the label, in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits a real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a Zero Mode Waveguide. In addition to their use in sequencing, the analogs and immobilized polymerases of the invention are also equally useful in a variety of other genotyping analyses, e.g., SNP genotyping using single base extension methods, real time monitoring of amplification, e.g., RT-PCR methods, and the like.

Further details regarding sequencing and nucleic acid amplification can be found in Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2005) ("Ausubel")) and *PCR Protocols A Guide to Methods and Applications* (Innis et al. eds) Academic Press Inc. San Diego, Calif. (1990) ("Innis").

Surfaces and Binding Partners

The surfaces of the invention can present a solid or semi-solid surface for any of a variety of linking chemistries that permit coupling of the binding partner to the surface. The binding partners coupled to the surfaces can be any of those noted herein, e.g., any partner that binds a surface coupling domain.

A wide variety of organic and inorganic polymers, both natural and synthetic may be employed as the material for the surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that may be employed include papers, ceramics, glass, metals, metalloids, semiconductive materials, cements, or the like. In addition, substances that form gels, such as proteins (e.g., gelatins), lipopolysaccharides, silicates, agarose and the like are also optionally used.

In several embodiments, the solid surface is a planar, substantially planar, or curved surface such as an array chip, a wall of an enzymatic reaction vessel such as a sequencing or amplification chamber, or the like. That is, in several embodiments the surface is other than a standard chromatographic medium used in standard affinity purification, e.g., other than a bead, column material, or gel.

A wide variety of linking chemistries are available for linking molecules constituting the binding partners to a wide variety of solid or semi-solid particle support elements. It is impractical and unnecessary to describe all of the possible known linking chemistries for linking molecules to a solid support. It is expected that one of skill can easily select appropriate chemistries, depending on the intended application.

In one preferred embodiment, the surfaces of the invention comprise silicate elements (e.g., glass or silicate surfaces). A variety of silicon-based molecules appropriate for functionalizing such surfaces are commercially available. See, for example, Silicon Compounds Registry and Review, United Chemical Technologies, Bristol, Pa. Additionally, the art in this area is very well developed and those of skill will be able to choose an appropriate molecule for a given purpose. Appropriate molecules can be purchased commercially, synthesized de novo, or can be formed by modifying an available molecule to produce one having the desired structure and/or characteristics.

The binding partner attaches to the solid substrate through any of a variety of chemical bonds. For example, the linker is optionally attached to the solid substrate using carbon-carbon bonds, for example via substrates having (poly)trifluorochloroethylene surfaces, or siloxane bonds (using, for example, glass or silicon oxide as the solid substrate). Siloxane bonds with the surface of the substrate are formed in one embodiment via reactions of derivatization reagents bearing trichlorosilyl or trialkoxysilyl groups. The particular linking group is selected based upon, e.g., its hydrophilic/hydrophobic properties where presentation of the binding partner in solution is desirable. Groups which are suitable for attachment to a linking group include amine, hydroxyl, thiol, carboxylic acid, ester, amide, isocyanate and isothiocyanate. Preferred derivatizing groups include aminoalkyltrialkoxysilanes, hydroxyalkyltrialkoxysilanes, polyethyleneglycols, polyethyleneimine, polyacrylamide, polyvinylalcohol and combinations thereof.

The binding partners that can be attached to a derivitized surface by these methods include peptides, nucleic acids, mimetics, large and small organic molecules, polymers and the like. The amino acids that are coupled in polypeptide binding partners can be either those having a structure that occurs naturally or they can be of unnatural structure (i.e., synthetic or unnatural, e.g., produced in a system of orthogonal components as noted above). Useful naturally occurring amino acids for coupling include, arginine, lysine, aspartic acid and glutamic acid. Surfaces that bind combinations of these amino acids are also of use in the present invention. Further, peptides comprising one or more residues having a charged or potentially charged side chain are useful binding partner components; these can be synthesized utilizing arginine, lysine, aspartic acid, glutamic acid and combinations thereof. Useful unnatural amino acids are commercially available or can be synthesized utilizing art-recognized methods. In those embodiments in which an amino acid moiety having an acidic or basic side chain is used, these moieties can be attached to a surface bearing a reactive group through standard peptide synthesis methodologies or easily accessible variations thereof. See, for example, Jones (1992), *Amino Acid and Peptide Synthesis*, Oxford University Press, Oxford.

Linking groups can also be incorporated into the binding partners of the invention. Linking groups of use in the present invention can have any of a range of structures, substituents and substitution patterns. They can, for example, be derivitized with nitrogen, oxygen and/or sulfur containing groups which are pendent from, or integral to, the linker group backbone. Examples include, polyethers, polyacids (polyacrylic acid, polylactic acid), polyols (e.g., glycerol), polyamines (e.g., spermine, spermidine) and molecules having more than one nitrogen, oxygen and/or sulfur moiety (e.g., 1,3-diamino-2-propanol, taurine). See, for example, Sandler et al. (1983) *Organic Functional Group Preparations* 2nd Ed., Academic Press, Inc. San Diego. A wide range of mono-, di- and bis-functionalized poly(ethyleneglycol) molecules are commercially available and will prove generally useful in this aspect of the invention. See, for example, 1997-1998 Catalog, Shearwater Polymers, Inc., Huntsville, Ala. Additionally, there are a number of easily practiced, useful modification strategies that can be applied to making linkers. See, for example, Harris, (1985) *Rev. Macromol. Chem. Phys., C*25(3), 325-373; Zalipsky et al., (1983) *Eur. Polym. J.,* 19(12), 1177-1183; U.S. Pat. No. 5,122,614, issued Jun. 16, 1992 to Zalipsky; U.S. Pat. No. 5,650,234, issued to Dolence et al. Jul. 22, 1997, and references therein.

In a preferred embodiment of the invention, the coupling chemistries for coupling binding partners to the surfaces of the invention are light-controllable, i.e., utilize photo-reactive chemistries. The use of photo-reactive chemistries and masking strategies to activate binding partner coupling to surfaces, as well as other photo-reactive chemistries is generally known (e.g., for semi-conductor chip fabrication and for coupling bio-polymers to solid phase materials). The use of photo-cleavable protecting groups and photo-masking permits type switching of both mobile and fixed array members, i.e., by altering the presence of substrates present on the array members (i.e., in response to light). Among a wide variety of protecting groups which are useful are nitroveratryl (NVOC)-methylnitroveratryl (Menvoc), allyloxycarbonyl (ALLOC), fluorenylmethoxycarbonyl (FMOC), -methylnitro-piperonyloxycarbonyl (MeNPOC), —NH-FMOC groups, t-butyl esters, t-butyl ethers, and the like. Various exemplary protecting groups (including both photo-cleavable and non-photocleavable groups) are described in, for example, Atherton et al., (1989) *Solid Phase Peptide Synthesis*, IRL Press, and Greene, et al. (1991) *Protective Groups In Organic Chemistry*, 2nd Ed., John Wiley & Sons, New York, N.Y., as well as, e.g., Fodor et al. (1991) Science, 251: 767-777, Wang (1976) J. Org. Chem. 41: 3258; and Rich, et al. (1975) J. Am. Chem. Soc. 97: 1575-1579.

Libraries

Polymerases bound to solid surfaces as described above can be formatted into libraries. The precise physical layout of these libraries is at the discretion of the practitioner. One can conveniently utilize gridded arrays of library members (e.g., individual bound polymerase enzymes, or blocks of polymerase enzyme types bound at fixed locations), e.g., on a glass or polymer surface, or formatted in a microtiter dish or other reaction vessel, or even dried on a substrate such as a membrane. However, other layout arrangements, are also appropriate, including those in which the library members are stored in separate locations that are accessed by one or more access control elements (e.g., that comprise a database of library member locations). The library format can be accessible by conventional robotics or microfluidic devices, or a combination thereof.

One common array format for use is a microtiter plate array, in which the library comprises an array embodied in the wells of a microtiter tray (or the components therein). The surfaces of the microtiter tray, or of beads located in the microtiter tray, provide two convenient implementations of libraries of surface-bound enzymes. Such trays are commercially available and can be ordered in a variety of well sizes and numbers of wells per tray, as well as with any of a variety of functionalized surfaces for binding of binding partners. Common trays include the ubiquitous 96 well plate, with 384 and 1536 well plates also in common use.

In addition to libraries that comprise liquid phase components, the libraries can also simply comprise solid phase arrays of enzymes (e.g., that can have liquid phase reagents added to them during operation). These arrays fix enzymes in a spatially accessible pattern (e.g., a grid of rows and columns) onto a solid substrate such as a membrane (e.g., nylon or nitrocellulose), a polymer or ceramic surface, a glass or modified silica surface, a metal surface, or the like.

While component libraries are most often thought of as physical elements with a specified spatial-physical relationship, the present invention can also make use of "logical" libraries, which do not have a straightforward spatial organization. For example, a computer system can be used to track the location of one or several components of interest which are located in or on physically disparate components. The computer system creates a logical library by providing a "look-up" table of the physical location of array members (e.g., using a commercially available inventory tracking system). Thus, even components in motion can be part of a logical library, as long as the members of the library can be specified and located.

Single Molecule Detection

The detection of activity of a single molecule of enzyme, or of a few proximal molecules, has a number of applications. For example, single molecule detection in sequencing applications can be used to dramatically reduce reagent consumption and to increase sequencing throughput. Detection of single molecule activity or of low numbers of molecules can similarly be used to reduce reagent consumption in other enzymatic assays.

In one example reaction of interest, a polymerase reaction can be isolated within an extremely small observation volume that effectively results in observation of individual polymerase molecules. As a result, the incorporation event provides observation of an incorporating nucleotide analog that is readily distinguishable from non-incorporated nucleotide analogs. In a preferred aspect, such small observation volumes are provided by immobilizing the polymerase enzyme within an optical confinement, such as a Zero Mode Waveguide. For a description of ZMWs and their application in single molecule analyses, and particularly nucleic acid sequencing, see the discussion above as well as, e.g., Levene et al., (2003) "Zero-mode waveguides for single-molecule analysis at high concentrations, Science 299:682-686, Published U.S. Patent Application No. 2003/0044781, and U.S. Pat. No. 6,917,726, each of which is incorporated herein by reference in its entirety for all purposes.

In one aspect, the polymerase includes a label, e.g., a fluorescent label. Such a label is optionally used to track the position of the polymerase in a ZMW. The label can be attached to the polymerase by any of a number of techniques known in the art; as just one example, a polymerase including a SNAP-tag can be labeled with a fluorophore by reaction with SNAP-vitro 488 or a similar compound (see, e.g., www(dot)covalys(dot)com).

Kits

Kits of the invention can take any of several different forms. For example, the surface bound enzymes can be provided as components of the kits, or the surface can be provided with binding partners suitable to bind the enzymes, which are optionally packaged separately. The kits can include packaging materials suitable to the application, e.g., with the enzymes of the invention packaged in a fashion to enable use of the enzymes. Regents that are relevant to enzyme function are optionally included as components of the kit, e.g., enzyme substrates, reaction buffers, or the like. Instructions for making or using surface bound enzymes are an optional feature of the invention.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a polymerase, or the amino acid sequence of a polymerase) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Polymerases or polymerase sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Current Protocols in Molecular Biology, Ausubel et al., eds., Current Protocols, a joint venture between Greene Publishing Associates, Inc. and John Wiley & Sons, Inc., supplemented through 2005).

EXAMPLES

It is understood that the examples and embodiments described herein are for illustrative purposes only and that various modifications or changes in light thereof will be suggested to persons skilled in the art and are features of the invention. Accordingly, the following examples are offered to illustrate, but not to limit, the claimed invention.

Example 1

Recombinant Polymerases

A vector for expression of a recombinant Phi 29 polymerase with three surface coupling domains was constructed and is schematically illustrated in FIG. 1. An N62D mutation was introduced into wild-type Phi 29 (SEQ ID NO:1) to reduce exonuclease activity, and GST (glutathione-5-transferase), His, and S tags were added as surface coupling domains. The resulting tagged N62D Phi 29 amino acid sequence is presented as SEQ ID NO:3. The sequence of the vector is presented as SEQ ID NO:8. The tagged N62D Phi 29 polymerase is encoded by nucleotides 4839-7428 of the vector sequence, with the polymerase at nucleotides 5700-7428 and the N62D mutation at nucleotides 5883-5885. The GST, His, and S tag surface coupling domains are encoded by nucleotides 4838-5699. Other features of the vector include the ribosome binding site (nucleotides 4822-4829), T7 promoter (nucleotides 4746-4758), and kanamycin resistance marker (complement of nucleotides 563-1375).

Additional mutations are readily introduced into this construct as desired, for example, to facilitate expression of recombinant Phi 29 polymerases having one or more of: a K135A mutation, an E375H mutation, an E375S mutation, an E375K mutation, an E375R mutation, an E375A mutation, an E375Q mutation, an E375W mutation, an E375Y mutation, an E375F mutation, an L384R mutation, an E486A mutation, an E486D mutation, a K512A mutation, a deletion of the NipTuck domain (residues 505-525), and a deletion within the NipTuck domain (within residues 505-525). These polymerases display modified properties relative to the wild-type for incorporation of nucleotide analogues. See, e.g., SEQ ID NOs:4-7. See also, "POLYMERASES FOR NUCLEOTIDE ANALOGUE INCORPORATION" by Hanzel et al., co-filed herewith and incorporated herein by reference in its entirety, and U.S. patent application 60/753,670 by Hanzel et al. entitled "POLYMERASES FOR NUCLEOTIDE ANALOGUE INCORPORATION" filed Dec. 22, 2005, and incorporated herein by reference in its entirety, which describes a variety of mutant Phi 29 polymerases. Similarly, wild-type Phi 29 having GST, His, and S tag surface coupling domains (SEQ ID NO:2) can be expressed from a similar construct. In one example, a 10-His tagged polymerase is provided, e.g., a 10-His tag is added to any polymerase herein or in U.S. patent application 60/753,670 by Hanzel et al. entitled "POLYMERASES FOR NUCLEOTIDE ANALOGUE INCORPORATION" filed Dec. 22, 2005 or in "POLYMERASES FOR NUCLEOTIDE ANALOGUE INCORPORATION" by Hanzel et al., co-filed herewith. As will be appreciated, the numbering of amino acid residues is with respect to the wild-type sequence of the Phi 29 polymerase, and actual position within a molecule of the invention may vary based upon the nature of the various modifications that the enzyme includes relative to the wild type Phi 29 enzyme, e.g., deletions and/or additions to the molecule, either at the termini or within the molecule itself.

The recombinant polymerase can be expressed in *E. coli*, for example, and purified using the GST, His, and/or S tags and standard techniques. The recombinant polymerase is optionally bound to a surface through one or more of the surface coupling domains. One or more of the GST, His, and S tags is optionally removed by digestion with an appropriate protease (e.g., thrombin or enterokinase, whose sites flank the S tag in the construct described above), for example, either following purification of the polymerase prior to coupling of the polymerase to a surface, or after coupling the polymerase to the surface in order to release the polymerase from the surface.

Further details regarding example polymerases, as well as additional example polymerases can be found in (co-filed) Hanzel et al. "POLYMERASES FOR NUCLEOTIDE ANALOGUE INCORPORATION", incorporated herein by reference for all purposes and in U.S. patent application 60/753,670 by Hanzel et al. entitled "POLYMERASES FOR NUCLEOTIDE ANALOGUE INCORPORATION" filed Dec. 22, 2005, also incorporated herein by reference for all purposes.

TABLE 1

Sequences of wild-type and exemplary recombinant polymerases.

| SEQ ID NO: | Notes | Sequence |
|---|---|---|
| 1 | wild-type Phi 29 amino acid sequence | MKHMPRKMYS CDFETTTKVE DCRVWAYGYM NIEDHSEYKI GNSLDEFMAW VLKVQADLYF HNLKFDGAFI INWLERNGFK WSADGLPNTY NTIISRMGQW YMIDICLGYK GKRKIHTVIY DSLKKLPFPV KKIAKDFKLT VLKGDIDYHK ERPVGYKITP EEYAYIKNDI QIIAEALLIQ PKQGLDRMTA GSDSLKGFKD IITTKKFKKV FPTLSLGLDK EVRYAYRGGF TWLNDRFKEK EIGEGMVFDV NSLYPAQMYS RLLPYGEPIV FEGKYVWDED YPLHIQHIRC EFELKEGYIP TIQIKRSRFY KGNEYLKSSG GEIADLWLSN VDLELMKEHY DLYNVEYISG LKFKATTGLF KDFIDKWTYI KTTSEGAIKQ LAKLMLNSLY GKFASNPDVT GKVPYLKENG ALGFRLGEEE TKDPVYTPMG VFITAWARYT TITAAQACYD RIIYCDTDSI HLTGTEIPDV IKDIVDPKKL GYWAHESTFK RAKYLRQKTY IQDIYMKEVD GKLVEGSPDD YTDIKFSVKC AGMTDKIKKE VTFENFKVGF SRKMKPKPVQ VPGGVVLVDD TFTIK |
| 2 | wild-type Phi 29 amino acid sequence (tagged) | mspilgywki kglvqptrll leyleekyee hlyerdegdk wrnkkfelgl efpnlpyyid gdvkltqsma iiryiadkhn mlggcpkera eismlegavl dirygvsria yskdfetlkv dflsklpeml kmfedrlchk tylngdhvth pdfmlydald vvlymdpmcl dafpklvcfk krieaipqid kylksskyia wplqgwqatf gggdhppksd gstsgsghhh hhhsaglvpr gstaigmket aaakferqhm dspdlgtggg sgddddkspm gyrgsefmkh mprkmyscdf etttkvedcr vwaygymnie dhseykigns ldefmawvlk vqadlyfhnl kfdgafiinw lerngfkwsa dglpntynti isrmgqwymi diclgykgkr kihtviydsl kklpfpvkki akdfkltvlk gdidyhkerp vgykitpeey ayikndiqii aealliqfkq gldrmtagsd slkgfkdiit tkkfkkvfpt lslgldkevr yayrggftwl ndrfkekeig egmvfdvnsl ypaqmysrll pygepivfeg kyvwdedypl hiqhircefe lkegyiptiq ikrsrfykgn eylkssggei adlwlsnvdl elmkehydly nveyisglkf kattglfkdf idkwtyiktt segaikqlak lmlnslygkf asnpdvtgkv pylkengalg frlgeeetkd pvytpmgvfi tawaryttit aaqacydrii ycdtdsihlt gteipdvikd ivdpkklgyw ahestfkrak ylrqktyiqd iymkevdgkl vegspddytd ikfsvkcagm tdkikkevtf enfkvgfsrk mkpkpvqvpg gvvlvddtft ik |
| 3 | N62D amino acid sequence (tagged) | mspilgywki kglvqptrll leyleekyee hlyerdegdk wrnkkfelgl efpnlpyyid gdvkltqsma iiryiadkhn mlggcpkera eismlegavl dirygvsria yskdfetlkv dflsklpeml kmfedrlchk tylngdhvth pdfmlydald vvlymdpmcl dafpklvcfk krieaipqid kylksskyia wplqgwqatf gggdhppksd gstsgsghhh hhhsaglvpr gstaigmket aaakferqhm dspdlgtggg sgddddkspm gyrgsefmkh mprkmyscdf |

TABLE 1-continued

Sequences of wild-type and exemplary recombinant polymerases.

| SEQ ID NO: | Notes | Sequence |
|---|---|---|
| | | etttkvedcr vwaygymnie dhseykigns ldefmawvlk vqadlyfhdl<br>kfdgafiinw lerngfkwsa dglpntynti isrmgqwymi diclgykgkr<br>kihtviydsl kklpfpvkki akdfkltvlk gdidyhkerp vgykitpeey<br>ayikndiqii aealliqfkq gldrmtagsd slkgfkdiit tkkfkkvfpt<br>lslgldkevr yayrggftwl ndrfkekeig egmvfdvnsl ypaqmysrll<br>pygepivfeg kyvwdedypl highircefe lkegyiptiq ikrsrfykgn<br>eylkssggei adlwlsnvdl elmkehydly nveyisglkf kattglfkdf<br>idkwtyiktt segaikqlak lmlnslygkf asnpdvtgkv pylkengalg<br>frlgeeetkd pvytpmgvfi tawaryttit aaqacydrii ycdtdsihlt<br>gteipdvikd ivdpkklgyw ahestfkrak ylrqktyiqd iymkevdgkl<br>vegspddytd ikfsvkcagm tdkikkevtf enfkvgfsrk mkpkpvqvpg<br>gvvlvddtft ik |
| 4 | L384R-N62D amino acid sequence (tagged) | mspilgywki kglvqptrll leyleekyee hlyerdegdk wrnkkfelgl<br>efpnlpyyid gdvkltqsma iiryiadkhn mlggcpkera eismlegavl<br>dirygvsria yskdfetlkv dflsklpeml kmfedrlchk tylngdhvth<br>pdfmlydald vvlymdpmcl dafpklvcfk krieaipqid kylksskyia<br>wplqgwqatf gggdhppksd gstsgsghhh hhhsaglvpr gstaigmket<br>aaakferqhm dspdlgtggg sgddddkspm gyrgsefmkh mprkmyscdf<br>etttkvedcr vwaygymnie dhseykigns ldefmawvlk vqadlyfhdl<br>kfdgafiinw lerngfkwsa dglpntynti isrmgqwymi diclgykgkr<br>kihtviydsl kklpfpvkki akdfkltvlk gdidyhkerp vgykitpeey<br>ayikndiqii aealliqfkq gldrmtagsd slkgfkdiit tkkfkkvfpt<br>lslgldkevr yayrggftwl ndrfkekeig egmvfdvnsl ypaqmysrll<br>pygepivfeg kyvwdedypl hiqhircefe lkegyiptiq ikrsrfykgn<br>eylkssggei adlwlsnvdl elmkehydly nveyisglkf kattglfkdf<br>idkwtyiktt segaikqlak rmlnslygkf asnpdvtgkv pylkengalg<br>frlgeeetkd pvytpmgvfi tawaryttit aaqacydrii ycdtdsihlt<br>gteipdvikd ivdpkklgyw ahestfkrak ylrqktyiqd iymkevdgkl<br>vegspddytd ikfsvkcagm tdkikkevtf enfkvgfsrk mkpkpvqvpg<br>gvvlvddtft ik |
| 5 | E486A-N62D amino acid sequence (tagged) | mspilgywki kglvqptrll leyleekyee hlyerdegdk wrnkkfelgl<br>efpnlpyyid gdvkltqsma iiryiadkhn mlggcpkera eismlegavl<br>dirygvsria yskdfetlkv dflsklpeml kmfedrlchk tylngdhvth<br>pdfmlydald vvlymdpmcl dafpklvcfk krieaipqid kylksskyia<br>wplqgwqatf gggdhppksd gstsgsghhh hhhsaglvpr gstaigmket<br>aaakferqhm dspdlgtggg sgddddkspm gyrgsefmkh mprkmyscdf<br>etttkvedcr vwaygymnie dhseykigns ldefmawvlk vqadlyfhdl<br>kfdgafiinw lerngfkwsa dglpntynti isrmgqwymi diclgykgkr<br>kihtviydsl kklpfpvkki akdfkltvlk gdidyhkerp vgykitpeey<br>ayikndiqii aealliqfkq gldrmtagsd slkgfkdiit tkkfkkvfpt<br>lslgldkevr yayrggftwl ndrfkekeig egmvfdvnsl ypaqmysrll<br>pygepivfeg kyvwdedypl hiqhircefe lkegyiptiq ikrsrfykgn<br>eylkssggei adlwlsnvdl elmkehydly nveyisglkf kattglfkdf<br>idkwtyiktt segaikqlak lmlnslygkf asnpdvtgkv pylkengalg<br>frlgeeetkd pvytpmgvfi tawaryttit aaqacydrii ycdtdsihlt<br>gteipdvikd ivdpkklgyw ahastfkrak ylrqktyiqd iymkevdgkl<br>vegspddytd ikfsvkcagm tdkikkevtf enfkvgfsrk mkpkpvqvpg<br>gvvlvddtft ik |
| 6 | E486D-N62D amino acid sequence (tagged) | mspilgywki kglvqptrll leyleekyee hlyerdegdk wrnkkfelgl<br>efpnlpyyid gdvkltqsma iiryiadkhn mlggcpkera eismlegavl<br>dirygvsria yskdfetlkv dflsklpeml kmfedrlchk tylngdhvth<br>pdfmlydald vvlymdpmcl dafpklvcfk krieaipqid kylksskyia<br>wplqgwqatf gggdhppksd gstsgsghhh hhhsaglvpr gstaigmket<br>aaakferqhm dspdlgtggg sgddddkspm gyrgsefmkh mprkmyscdf<br>etttkvedcr vwaygymnie dhseykigns ldefmawvlk vqadlyfhdl<br>kfdgafiinw lerngfkwsa dglpntynti isrmgqwymi diclgykgkr<br>kihtviydsl kklpfpvkki akdfkltvlk gdidyhkerp vgykitpeey<br>ayikndiqii aealliqfkq gldrmtagsd slkgfkdiit tkkfkkvfpt<br>lslgldkevr yayrggftwl ndrfkekeig egmvfdvnsl ypaqmysrll<br>pygepivfeg kyvwdedypl hiqhircefe lkegyiptiq ikrsrfykgn<br>eylkssggei adlwlsnvdl elmkehydly nveyisglkf kattglfkdf<br>idkwtyiktt segaikqlak lmlnslygkf asnpdvtgkv pylkengalg<br>frlgeeetkd pvytpmgvfi tawaryttit aaqacydrii ycdtdsihlt<br>gteipdvikd ivdpkklgyw andstfkrak ylrqktyiqd iymkevdgkl<br>vegspddytd ikfsvkcagm tdkikkevtf enfkvgfsrk mkpkpvgvpg<br>gvvlvddtft ik |
| 7 | K512A-N62D amino acid sequence (tagged) | mspilgywki kglvqptrll leyleekyee hlyerdegdk wrnkkfelgl<br>efpnlpyyid gdvkltqsma iiryiadkhn mlggcpkera eismlegavl<br>dirygvsria yskdfetlkv dflsklpeml kmfedrlchk tylngdhvth<br>pdfmlydald vvlymdpmcl dafpklvcfk krieaipqid kylksskyia<br>wplqgwqatf gggdhppksd gstsgsghhh hhhsaglvpr gstaiymket<br>aaakferghm dspdlgtggg sgddddkspm gyrgsefmkh mprkmyscdf |

TABLE 1-continued

Sequences of wild-type and exemplary recombinant polymerases.

| SEQ ID NO: | Notes | Sequence |
|---|---|---|
|  |  | etttkvedcr vwaygymnie dhseykigns ldefmawvlk vqadlyfhdl<br>kfdgafiinw lerngfkwsa dglpntynti isrmgqwymi diclgykgkr<br>kihtviydsl kklpfpvkki akdfkltvlk gdidyhkerp vgykitpeey<br>ayikndigii aealliqfkq gldrmtagsd slkgfkdiit tkkfkkvfpt<br>lslgldkevr yayrggftwl ndrfkekeig egmvfdvnsl ypaqmysrll<br>pygepivfeg kyvwdedypl hiqhircefe lkegyiptiq ikrsrfykgn<br>eylkssggei adlwlsnvdl elmkehydly nveyisglkf kattglfkdf<br>idkwtyiktt segaikqlak lmlnslygkf asnpdvtgkv pylkengalg<br>frlgeeetkd pvytpmgvfi tawaryttit aagacydrii ycdtdsihlt<br>gteipdvikd ivdpkklgyw ahestfkrak ylrqktyiqd iymkevdgal<br>vegspddytd ikfsvkcagm tdkikkevtf enfkvgfsrk mkpkpvgvpg<br>gvvlvddtft ik |
| 8 | N62D nucleotide sequence-pET41 N62D 1 plasmid | tggcgaatgggacgcgccctgtagcggcgcattaagcgcggcgggtgtggtggt<br>tacgcgcagcgtgaccgctacacttgccagcgccctagcgcccgctcctttcgc<br>tttcttcccttcctttctcgccacgttcgccggctttccccgtcaagctctaaa<br>tcggggctccctttagggttccgatttagtgctttacggcacctcgacccccaa<br>aaaacttgattagggtgatggttcacgtagtgggccatcgcctgatagacggt<br>ttttcgcccttgacgttggagtccacgttctttaatagtggactcttgttcca<br>aactggaacaacactcaaccctatctcggtctattctttgatttataagggat<br>tttgccgatttcggcctattggttaaaaaatgagctgatttaacaaaaatttaa<br>cgcgaatttttaacaaaatattaacgtttacaatttcaggtggcacttttcgggg<br>aaatgtgcgcggaacccctatttgtttattttctaaatacattcaaatatgta<br>tccgctcatgaattaattcttagaaaaactcatcgagcatcaaatgaaactgca<br>atttattcatatcaggattatcaataccatattttgaaaaagccgtttctgta<br>atgaaggagaaaactcaccgaggcagttccataggatggcaagatcctggtatc<br>ggtctgcgattccgactcgtccaacatcaatacaacctattaatttcccctcgt<br>caaaaataaggttatcaagtgagaaatcaccatgagtgacgactgaatccggtg<br>agaatggcaaaagtttatgcatttctttccagacttgttcaacaggccagccat<br>tacgctcgtcatcaaaatcactcgcatcaaccaaaccgttattcattcgtgatt<br>gcgcctgagcgagacgaaatacgcgatcgctgttaaaaggacaattacaaacag<br>gaatcgaatgcaaccggcgcaggaacactgccagcgcatcaacaatattttcac<br>ctgaatcaggatattcttctaatacctggaatgctgttttccggggatcgcag<br>tggtgagtaaccatgcatcatcaggagtacggataaaatgcttgatggtcggaa<br>gaggcataaaattccgtcagccagtttagtctgaccatctcatctgtaacatcat<br>tggcaacgctacctttgccatgtttcagaaacaactctggcgcatcgggcttcc<br>catacaatcgatagattgtcgcacctgattgcccgacattatcgcgagcccatt<br>tatacccatataaatcagcatccatgttggaatttaatcgcggcctagagcaag<br>acgtttcccgttgaatatggctcataacacccccttgtattactgtttatgtaag<br>cagacagttttattgttcatgaccaaaatcccttaacgtgagttttcgttccac<br>tgagcgtcagacccgtagaaaagatcaaggatcttcttgagatcctttttt<br>ctgcgcgtaatctgctgcttgcaaacaaaaaaaccaccgctaccagcggtggtt<br>tgtttgccggatcaagagctaccaactctttttccgaaggtaactggcttcagc<br>agagcgcagataccaaatactgtccttctagtgtagccgtagttaggccaccac<br>ttcaagaactctgtagcaccgcctacatacctcgctctgctaatcctgttacca<br>gtggctgctgccagtggcgataagtcgtgtcttaccgggttggactcaagacga<br>tagttaccggataaggcgcagcggtcgggctgaacggggggttcgtgcacacag<br>cccagcttggagcgaacgacctacaccgaactgagatacctacagcgtgagcta<br>tgagaaagcgccacgcttcccgaagggagaaaggcggacaggtatccggtaagc<br>ggcagggtcggaacaggagagcgcacgagggagcttccaggggggaaacgcctgg<br>tatctttatagtcctgtcgggtttcgccacctctgacttgagcgtcgattttg<br>tgatgctcgtcaggggggcggagcctatggaaaaacgccagcaacgcggcctt<br>ttacggttcctggccttttgctggccttttgctcacatgttctttcctgcgtta<br>tcccctgattctgtggataaccgtattaccgcctttgagtgagctgataccgct<br>cgccgcagccgaacgaccgagcgcagcgagtcagtgagcgaggaagcggaagag<br>cgcctgatgcggtattttctccttacgcatctgtgcggtatttcacaccgcata<br>tatggtgcactctcagtacaatctgctctgatgccgcatagttaagccagtata<br>cactccgctatcgctacgtgactgggtcatggctgcgccccgacacccgccaac<br>acccgctgacgcgccctgacgggcttgtctgctcccggcatccgcttacagaca<br>agctgtgaccgtctccgggagctgcatgtgtcagaggttttcaccgtcatcacc<br>gaaacgcgcgaggcagctgcggtaaagctcatcagcgtggtcgtgaagcgattc<br>acagatgtctgcctgttcatccgcgtccagctcgttgagtttctccagaagcgt<br>taatgtctggcttctgataaagcgggccatgttaagggcggttttttcctgttt<br>ggtcactgatgcctccgtgtaaggggggatttctgttcatgggggtaatgatacc<br>gatgaaacgagagaggatgctcacgatacgggttactgatgatgaacatgcccg<br>gttactggaacgttgtgagggtaaacaactggcggtatggatgcggcgggacca<br>gagaaaaatcactcagggtcaatgccagcgcttcgttaatacagatgtaggtgt<br>tccacagggtagccagcagcatcctgcgatgcagatccggaacataatggtgca<br>gggcgctgacttccgcgtttccagactttacgaaacacggaaaccgaagaccat<br>tcatgttgttgctcaggtcgcagacgttttgcagcagcagtcgcttcacgttcg<br>ctcgcgtatcggtgattcattctgctaaccagtaaggcaaccccgccagcctag<br>ccgggtcctcaacgacaggagcacgatcatgctagtcatgccccgcgcccaccg<br>gaaggagctgactgggttgaaggctctcaagggcatcggtcgagatcccggtgc<br>ctaatgagtgagctaacttacattaattgcgttgcgctcactgcccgctttcca<br>gtcggaaacctgtcgtgccagctgcattaatgaatcggccaacgcgcgggag<br>aggcggtttgcgtattgggcgccagggtggttttttctttcaccagtgagacgg |

TABLE 1-continued

Sequences of wild-type and exemplary recombinant polymerases.

| SEQ ID NO: Notes | Sequence |
|---|---|
| | gcaacagctgattgcccttcaccgcctggccctgagagagttgcagcaagcggt
ccacgctggtttgcccagcaggcgaaaatcctgtttgatggtggttaacggcg
ggatataacatgagctgtcttcggtatcgtcgtatcccactaccgagatgtccg
caccaacgcgcagcccggactcggtaatggcgcgcattgcgcccagcgccatct
gatcgttggcaaccagcatcgcagtgggaacgatgccctcattcagcatttgca
tggtttgttgaaaaccggacatggcactccagtcgccttcccgttccgctatcg
gctgaatttgattgcgagtgagatatttatgccagccagccagacgcagacgcg
ccgagacagaacttaatgggcccgctaacagcgcgatttgctggtgacccaatg
cgaccagatgctccacgcccagtcgcgtaccgtcttcatgggagaaaataatac
tgttgatgggtgtctggtcagagacatcaagaaataacgccggaacattagtgc
aggcagcttccacagcaatggcatcctggtcatccagcggatagttaatgatca
gcccactgacgcgttgcgcgagaagattgtgcaccgccgctttacaggcttcga
cgccgcttcgttctaccatcgacaccaccacgctggcacccagttgatcggcgc
gagatttaatcgccgcgacaatttgcgacggcgcgtgcagggccagactggagg
tggcaacgccaatcagcaacgactgtttgcccgccagttgttgtgccacgcggt
tgggaatgtaattcagctccgccatcgccgcttccacttttttcccgcgttttcg
cagaaacgtggctggcctggttcaccacgcgggaaacggtctgataagagacac
cggcatactctgcgacatcgtataacgttactggtttcacattcaccaccctga
attgactctcttccgggcgctatcatgccataccgcgaaaggttttgcgccatt
cgatggtgtccgggatctcgacgctctcccttatgcgactcctgcattaggaag
cagcccagtagtaggttgaggccgttgagcaccgccgccgcaaggaatggtgca
tgcaaggagatggcgcccaacagtccccggccacggggcctgccaccatacc
acgccgaaacaagcgctcatgagcccgaagtggcgagcccgatcttccccatcg
gtgatgtcggcgatataggcgccagcaaccgcacctgtggcgccggtgatgccg
gccacgatgcgtccggcgtagaggatcgagatcgatctcgatcccgcgaaatta
atacgactcactataggggaattgtgagcggataacaattcccctctagaaata
attttgtttaactttaagaaggagatatacatatgtccctatactaggttatt
ggaaaattaagggccttgtgcaacccactcgacttcttttggaatatcttgaag
aaaaatatgaagagcatttgtatgagcgcgatgaaggtgataaatggcgaaaca
aaaagtttgaatttgggtttggagtttcccaatcttccttattatattgatggtg
atgttaaattaacacagtctatggccatcatacgttatatagctgacaagcaca
acatgttgggtggttgtccaaaagagcgtgcagagatttcaatgcttgaaggag
cggttttggatattagatacggtgtttcgagaattgcatatagtaaagactttg
aaactctcaaagttgattttcttagcaagctacctgaaatgctgaaaatgttcg
aagatcgttatgtcataaaacatatttaaatggtgatcatgtaacccatcctg
acttcatgttgtatgacgctcttgatgttgttttatacatggacccaatgtgcc
tggatgcgttcccaaaattagtttgttttaaaaaacgtattgaagctatcccac
aaattgataagtacttgaaatccagcaagtatatagcatggcctttgcagggct
ggcaagccacgtttggtggtggcgaccatcctccaaaatcggatggttcaacta
gtggttctggtcatcaccatcaccatcactccgcgggtctggtgccacgcggta
gtactgcaattggtatgaaagaaaccgctgctgctaaattcgaacgccagcaca
tggacagcccagatctgggtaccggtggtggctccggtgatgacgacgacaaga
gtcccatgggatatcggggatccgaattcatgaagcatatgccgagaaagatgt
atagttgtgactttgagacaactactaaagtggaagactgtagggtatgggcgt
atggttatatgaatatagaagatcacagtgagtacaaaataggtaatagcctgg
atgagtttatggcgtgggtgttgaaggtacaagctgatctatattccatgatc
tcaaatttgacggagctttttatcattaactggttggaacgtaatggttttaagt
ggtcggctgacggattgccaaacacatataatacgatcatatctcgcatgggac
aatggtacatgattgatatatgtttaggctacaaagggaaacgtaagatacata
cagtgatatatgacagcttaaagaaactaccgtttcctgttaagaagatagcta
aagactttaaactaactgttcttaaaggtgatattgattaccacaaagaaagac
cagtcggctataagataacacccgaagaatacgcctatattaaaaacgatattc
agattattgcggaagctctgttaattcagtttaagcaaggtttagaccggatga
cagcaggcagtgacagtctaaaaggtttcaaggatattataaccactaagaaat
tcaaaaaggtgtttcctacattgagtcttggactcgataaggaagtgagatacg
cctatagaggtggttttacatggttaaatgataggttcaaagaaaaagaaatcg
gagaaggcatggtcttcgatgttaatagtctatatcctgcacagatgtatagtc
gtctccttccatatggtgaacctatagtattcgagggtaaatacgtttgggacg
aagattaccctactacacatacagcatatcagatgtgagttcgaattgaaagagg
gctatataccca ctatacagataaaaagaagtaggttttataaaggtaatgag
tacctaaaaagtagcggcggggagatagccgacctctggttgtcaaatgtgagac
ctagaattaatgaaagaacactacgatttatataacgttgaatatatcagcggc
ttaaaatttaaagcaactacaggtttgtttaaagattttatagataaatggacg
tacatcaagacgacatcagaaggagcgatcaagcaactagcaaaactgatgtta
aacagtctatacggtaaattcgctagtaaccctgatgttacagggaaagtccct
tatttaaaagagaatggggcgctaggtttcagacttggagaagaggaaacaaaa
gaccctgtttatacacctatgggcgttttcatcactgcatgggctagatacacg
acaattacagcggcacaggcttgttatgatcggataatatactgtgatactgac
agcatacatttaacgggtacagagatacctgatgtaataaaagatatagttgac
cctaagaaatttgggatactgggcacatgaaagtacattcaaaagagctaaatat
ctgagacagaagacctatatacaagacatctatatgaaagaagtagatggtaag
ttagtagaaggtagtccagatgattacactgatataaaatttagtgttaaatgt
gcgggaatgactgacaagattaagaaagaggttacgtttgagaatttcaaagtc
ggattcagtcggaaaatgaagcctaagcctgtgcaagtgccgggcggggtggtt
ctggttgatgacacattcacaatcaaataagaattctgtacaggccttggcgcg
cctgcaggcgagctccgtcgacaagcttgcggccgcactcgagcaccaccacca |

TABLE 1-continued

Sequences of wild-type and exemplary recombinant polymerases.

| SEQ ID NO: | Notes | Sequence |
|---|---|---|
| | | ccaccaccaccactaattgattaatacctaggctgctaaacaaagcccgaaagg aagctgagttggctgctgccaccgctgagcaataactagcataacccccttgggg cctctaaacgggtcttgagggggttttttgctgaaaggaggaactatatccggat |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. An isolated or recombinant DNA polymerase bound to a solid surface, the polymerase comprising:
an active site; and,
an artificial or recombinant surface coupling domain, wherein the surface coupling domain is distal to the active site;
wherein the polymerase comprises an amino acid sequence that is at least 80% identical to SEQ ID NO: 1 and that comprises at least one mutation selected from the group consisting of an E375H mutation, an E375S mutation, an E375K mutation, an E375R mutation, an E375A mutation, an E375Q mutation, an E375W mutation, an E375Y mutation, an E375F mutation, and a K512A mutation, wherein identification of positions is relative to SEQ ID NO:1; wherein the surface coupling domain comprises: a biotin, a biotinylatable polypeptide sequence, an avidin sequence, a AviTag sequence, a recombinant dimer domain of the protein, a large extraneous polypeptide domain, a GST sequence, a glutathione, an S tag, a recombinant polymerase domain, or a combination thereof; wherein the surface coupling domain is bound to a binding partner that is coupled or bound to the solid surface, whereby the polymerase is bound to the solid surface; wherein the polymerase is capable of catalyzing a polymerization reaction while bound to the solid surface; and wherein the polymerase, when bound to the surface, displays a kcat/Km that is at least 10% as high as a corresponding DNA polymerase in solution;
wherein the surface comprises or is proximal to a zero mode waveguide.

2. The isolated or recombinant DNA polymerase of claim 1, wherein the polymerase comprises a deletion in one or more editing domain of the polymerase, whereby the polymerase displays reduced or eliminated exonuclease activity.

3. The isolated or recombinant DNA polymerase of claim 1, wherein the polymerase comprises exonuclease activity.

4. The isolated or recombinant DNA polymerase of claim 1, wherein the polymerase comprises an amino acid sequence that is at least 90% identical to SEQ ID NO: 1.

5. The isolated or recombinant DNA polymerase of claim 1, wherein the DNA polymerase comprises an E375Y mutation.

6. The isolated or recombinant DNA polymerase of claim 1, wherein the artificial surface coupling domain comprises at least one purification tag.

7. The isolated or recombinant DNA polymerase of claim 1, wherein the polymerase comprises two or more surface coupling domains.

8. The isolated or recombinant DNA polymerase of claim 1, wherein the surface coupling domain is at least 5 kDa in size.

9. The isolated or recombinant DNA polymerase of claim 1, wherein the surface coupling domain is at least 10 kDa in size.

10. The isolated or recombinant DNA polymerase of claim 1, wherein the surface coupling domain is at least 50 kDa in size.

11. The isolated or recombinant DNA polymerase of claim 1, wherein the surface coupling domain is at least 100 kDa in size.

12. The isolated or recombinant DNA polymerase of claim 1, wherein the artificial surface coupling domain is located within an N-terminal domain of the polymerase.

13. The isolated or recombinant DNA polymerase of claim 1, wherein binding of the polymerase to a surface by the surface coupling domain orients the polymerase relative to the surface.

14. The isolated or recombinant DNA polymerase of claim 1, wherein a location of the polymerase on the surface is fixed, thereby providing a spatial address of the polymerase on the surface.

15. The isolated or recombinant DNA polymerase of claim 1, wherein the surface comprises glass, a slide, or a combination thereof.

16. The isolated or recombinant DNA polymerase of claim 1, wherein the polymerase, when bound to the surface, displays a $k_{cat}/K_m$ that is at least 50% as high as a corresponding DNA polymerase in solution.

17. The isolated or recombinant DNA polymerase of claim 1, wherein the polymerase, when bound to the surface, displays a $k_{cat}/K_m$ that is at least 75% as high as a corresponding DNA polymerase in solution.

18. The isolated or recombinant DNA polymerase of claim 1, wherein the polymerase is coupled to the surface in a fixed orientation relative to the surface.

19. The isolated or recombinant DNA polymerase of claim 18, wherein the fixed orientation results in an active site of the polymerase being distal to the surface.

20. The isolated or recombinant DNA polymerase of claim 1, wherein the surface coupling domain comprises a biotin, a biotinylatable polypeptide sequence, or a combination thereof.

* * * * *

SEQUENCE LISTING

<160> NUMBER OF SEQ ID NOS: 8

<210> SEQ ID NO 1
<211> LENGTH: 575
<212> TYPE: PRT
<213> ORGANISM: Bacteriophage phi-29

<400> SEQUENCE: 1

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255
```

```
Gln Met Tyr Ser Arg Leu Leu Pro Tyr Gly Glu Pro Ile Val Phe Glu
        260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Thr Lys Asp Pro Val Tyr Thr Pro Met Gly Val Phe Ile
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Glu Val Thr Phe Glu
        530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 2
<211> LENGTH: 862
<212> TYPE: PRT
<213> ORGANISM: Artificial
<220> FEATURE:
<223> OTHER INFORMATION: GST, His, and S-tagged Phi29 polymerase

<400> SEQUENCE: 2

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45
```

```
Gly Leu Glu Phe Pro Asn Leu Pro Tyr Tyr Ile Asp Gly Val Lys
         50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                     85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
                195                 200                 205
Thr Phe Gly Gly Asp His Pro Pro Lys Ser Asp Gly Ser Thr Ser
        210                 215                 220
Gly Ser Gly His His His His His His Ser Ala Gly Leu Val Pro Arg
225                 230                 235                 240
Gly Ser Thr Ala Ile Gly Met Lys Glu Thr Ala Ala Lys Phe Glu
                245                 250                 255
Arg Gln His Met Asp Ser Pro Asp Leu Gly Thr Gly Gly Gly Ser Gly
            260                 265                 270
Asp Asp Asp Asp Lys Ser Pro Met Gly Tyr Arg Gly Ser Glu Phe Met
            275                 280                 285
Lys His Met Pro Arg Lys Met Tyr Ser Cys Asp Phe Glu Thr Thr Thr
            290                 295                 300
Lys Val Glu Asp Cys Arg Val Trp Ala Tyr Gly Tyr Met Asn Ile Glu
305                 310                 315                 320
Asp His Ser Glu Tyr Lys Ile Gly Asn Ser Leu Asp Glu Phe Met Ala
                325                 330                 335
Trp Val Leu Lys Val Gln Ala Asp Leu Tyr Phe His Asn Leu Lys Phe
                340                 345                 350
Asp Gly Ala Phe Ile Ile Asn Trp Leu Glu Arg Asn Gly Phe Lys Trp
            355                 360                 365
Ser Ala Asp Gly Leu Pro Asn Thr Tyr Asn Thr Ile Ile Ser Arg Met
370                 375                 380
Gly Gln Trp Tyr Met Ile Asp Ile Cys Leu Gly Tyr Lys Gly Lys Arg
385                 390                 395                 400
Lys Ile His Thr Val Ile Tyr Asp Ser Leu Lys Lys Leu Pro Phe Pro
                405                 410                 415
Val Lys Lys Ile Ala Lys Asp Phe Lys Leu Thr Val Leu Lys Gly Asp
                420                 425                 430
Ile Asp Tyr His Lys Glu Arg Pro Val Gly Tyr Lys Ile Thr Pro Glu
            435                 440                 445
Glu Tyr Ala Tyr Ile Lys Asn Asp Ile Gln Ile Ile Ala Glu Ala Leu
450                 455                 460
```

-continued

```
Leu Ile Gln Phe Lys Gln Gly Leu Asp Arg Met Thr Ala Gly Ser Asp
465                 470                 475                 480

Ser Leu Lys Gly Phe Lys Asp Ile Ile Thr Thr Lys Lys Phe Lys Lys
            485                 490                 495

Val Phe Pro Thr Leu Ser Leu Gly Leu Asp Lys Glu Val Arg Tyr Ala
        500                 505                 510

Tyr Arg Gly Gly Phe Thr Trp Leu Asn Asp Arg Phe Lys Glu Lys Glu
    515                 520                 525

Ile Gly Glu Gly Met Val Phe Asp Val Asn Ser Leu Tyr Pro Ala Gln
530                 535                 540

Met Tyr Ser Arg Leu Leu Pro Tyr Gly Glu Pro Ile Val Phe Glu Gly
545                 550                 555                 560

Lys Tyr Val Trp Asp Glu Asp Tyr Pro Leu His Ile Gln His Ile Arg
            565                 570                 575

Cys Glu Phe Glu Leu Lys Glu Gly Tyr Ile Pro Thr Ile Gln Ile Lys
        580                 585                 590

Arg Ser Arg Phe Tyr Lys Gly Asn Glu Tyr Leu Lys Ser Ser Gly Gly
    595                 600                 605

Glu Ile Ala Asp Leu Trp Leu Ser Asn Val Asp Leu Glu Leu Met Lys
610                 615                 620

Glu His Tyr Asp Leu Tyr Asn Val Glu Tyr Ile Ser Gly Leu Lys Phe
625                 630                 635                 640

Lys Ala Thr Thr Gly Leu Phe Lys Asp Phe Ile Asp Lys Trp Thr Tyr
            645                 650                 655

Ile Lys Thr Thr Ser Glu Gly Ala Ile Lys Gln Leu Ala Lys Leu Met
        660                 665                 670

Leu Asn Ser Leu Tyr Gly Lys Phe Ala Ser Asn Pro Asp Val Thr Gly
    675                 680                 685

Lys Val Pro Tyr Leu Lys Glu Asn Gly Ala Leu Gly Phe Arg Leu Gly
690                 695                 700

Glu Glu Glu Thr Lys Asp Pro Val Tyr Thr Pro Met Gly Val Phe Ile
705                 710                 715                 720

Thr Ala Trp Ala Arg Tyr Thr Thr Ile Thr Ala Ala Gln Ala Cys Tyr
            725                 730                 735

Asp Arg Ile Ile Tyr Cys Asp Thr Asp Ser Ile His Leu Thr Gly Thr
        740                 745                 750

Glu Ile Pro Asp Val Ile Lys Asp Ile Val Asp Pro Lys Lys Leu Gly
    755                 760                 765

Tyr Trp Ala His Glu Ser Thr Phe Lys Arg Ala Lys Tyr Leu Arg Gln
770                 775                 780

Lys Thr Tyr Ile Gln Asp Ile Tyr Met Lys Glu Val Asp Gly Lys Leu
785                 790                 795                 800

Val Glu Gly Ser Pro Asp Asp Tyr Thr Asp Ile Lys Phe Ser Val Lys
            805                 810                 815

Cys Ala Gly Met Thr Asp Lys Ile Lys Lys Glu Val Thr Phe Glu Asn
        820                 825                 830

Phe Lys Val Gly Phe Ser Arg Lys Met Lys Pro Lys Pro Val Gln Val
    835                 840                 845

Pro Gly Gly Val Val Leu Val Asp Asp Thr Phe Thr Ile Lys
850                 855                 860

<210> SEQ ID NO 3
<211> LENGTH: 862
<212> TYPE: PRT
```

<213> ORGANISM: Artificial
<220> FEATURE:
<223> OTHER INFORMATION: GST, His, and S-tagged N62D mutant Phi29 polymerase

<400> SEQUENCE: 3

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Asp Lys Ser Pro Met Gly Tyr Arg Gly Ser Glu Phe Met
        275                 280                 285

Lys His Met Pro Arg Lys Met Tyr Ser Cys Asp Phe Glu Thr Thr Thr
    290                 295                 300

Lys Val Glu Asp Cys Arg Val Trp Ala Tyr Gly Tyr Met Asn Ile Glu
305                 310                 315                 320

Asp His Ser Glu Tyr Lys Ile Gly Asn Ser Leu Asp Glu Phe Met Ala
                325                 330                 335

Trp Val Leu Lys Val Gln Ala Asp Leu Tyr Phe His Asp Leu Lys Phe
            340                 345                 350

Asp Gly Ala Phe Ile Ile Asn Trp Leu Glu Arg Asn Gly Phe Lys Trp
        355                 360                 365

Ser Ala Asp Gly Leu Pro Asn Thr Tyr Asn Thr Ile Ile Ser Arg Met
    370                 375                 380
```

```
Gly Gln Trp Tyr Met Ile Asp Ile Cys Leu Gly Tyr Lys Gly Lys Arg
385                 390                 395                 400

Lys Ile His Thr Val Ile Tyr Asp Ser Leu Lys Lys Leu Pro Phe Pro
            405                 410                 415

Val Lys Lys Ile Ala Lys Asp Phe Lys Leu Thr Val Leu Lys Gly Asp
            420                 425                 430

Ile Asp Tyr His Lys Glu Arg Pro Val Gly Tyr Lys Ile Thr Pro Glu
            435                 440                 445

Glu Tyr Ala Tyr Ile Lys Asn Asp Ile Gln Ile Ile Ala Glu Ala Leu
450                 455                 460

Leu Ile Gln Phe Lys Gln Gly Leu Asp Arg Met Thr Ala Gly Ser Asp
465                 470                 475                 480

Ser Leu Lys Gly Phe Lys Asp Ile Ile Thr Thr Lys Lys Phe Lys Lys
            485                 490                 495

Val Phe Pro Thr Leu Ser Leu Gly Leu Asp Lys Glu Val Arg Tyr Ala
            500                 505                 510

Tyr Arg Gly Gly Phe Thr Trp Leu Asn Asp Arg Phe Lys Glu Lys Glu
            515                 520                 525

Ile Gly Glu Gly Met Val Phe Asp Val Asn Ser Leu Tyr Pro Ala Gln
530                 535                 540

Met Tyr Ser Arg Leu Leu Pro Tyr Gly Glu Pro Ile Val Phe Glu Gly
545                 550                 555                 560

Lys Tyr Val Trp Asp Glu Asp Tyr Pro Leu His Ile Gln His Ile Arg
            565                 570                 575

Cys Glu Phe Glu Leu Lys Glu Gly Tyr Ile Pro Thr Ile Gln Ile Lys
            580                 585                 590

Arg Ser Arg Phe Tyr Lys Gly Asn Glu Tyr Leu Lys Ser Ser Gly Gly
            595                 600                 605

Glu Ile Ala Asp Leu Trp Leu Ser Asn Val Asp Leu Glu Leu Met Lys
610                 615                 620

Glu His Tyr Asp Leu Tyr Asn Val Glu Tyr Ile Ser Gly Leu Lys Phe
625                 630                 635                 640

Lys Ala Thr Thr Gly Leu Phe Lys Asp Phe Ile Asp Lys Trp Thr Tyr
            645                 650                 655

Ile Lys Thr Thr Ser Glu Gly Ala Ile Lys Gln Leu Ala Lys Leu Met
            660                 665                 670

Leu Asn Ser Leu Tyr Gly Lys Phe Ala Ser Asn Pro Asp Val Thr Gly
            675                 680                 685

Lys Val Pro Tyr Leu Lys Glu Asn Gly Ala Leu Gly Phe Arg Leu Gly
690                 695                 700

Glu Glu Glu Thr Lys Asp Pro Val Tyr Thr Pro Met Gly Val Phe Ile
705                 710                 715                 720

Thr Ala Trp Ala Arg Tyr Thr Thr Ile Thr Ala Ala Gln Ala Cys Tyr
            725                 730                 735

Asp Arg Ile Ile Tyr Cys Asp Thr Asp Ser Ile His Leu Thr Gly Thr
            740                 745                 750

Glu Ile Pro Asp Val Ile Lys Asp Ile Val Asp Pro Lys Lys Leu Gly
            755                 760                 765

Tyr Trp Ala His Glu Ser Thr Phe Lys Arg Ala Lys Tyr Leu Arg Gln
            770                 775                 780

Lys Thr Tyr Ile Gln Asp Ile Tyr Met Lys Glu Val Asp Gly Lys Leu
785                 790                 795                 800

Val Glu Gly Ser Pro Asp Asp Tyr Thr Asp Ile Lys Phe Ser Val Lys
```

```
                805                 810                 815
Cys Ala Gly Met Thr Asp Lys Ile Lys Lys Glu Val Thr Phe Glu Asn
            820                 825                 830

Phe Lys Val Gly Phe Ser Arg Lys Met Lys Pro Lys Pro Val Gln Val
        835                 840                 845

Pro Gly Gly Val Val Leu Val Asp Asp Thr Phe Thr Ile Lys
    850                 855                 860

<210> SEQ ID NO 4
<211> LENGTH: 862
<212> TYPE: PRT
<213> ORGANISM: Artificial
<220> FEATURE:
<223> OTHER INFORMATION: GST, His, and S-tagged L384R-N62D mutant Phi29
      polymerase

<400> SEQUENCE: 4

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Lys Phe Glu
                245                 250                 255

Arg Gln His Met Asp Ser Pro Asp Leu Gly Thr Gly Gly Ser Gly
            260                 265                 270

Asp Asp Asp Asp Lys Ser Pro Met Gly Tyr Arg Gly Ser Glu Phe Met
        275                 280                 285

Lys His Met Pro Arg Lys Met Tyr Ser Cys Asp Phe Glu Thr Thr Thr
    290                 295                 300
```

-continued

```
Lys Val Glu Asp Cys Arg Val Trp Ala Tyr Gly Tyr Met Asn Ile Glu
305                 310                 315                 320

Asp His Ser Glu Tyr Lys Ile Gly Asn Ser Leu Asp Glu Phe Met Ala
            325                 330                 335

Trp Val Leu Lys Val Gln Ala Asp Leu Tyr Phe His Asp Leu Lys Phe
                340                 345                 350

Asp Gly Ala Phe Ile Ile Asn Trp Leu Glu Arg Asn Gly Phe Lys Trp
            355                 360                 365

Ser Ala Asp Gly Leu Pro Asn Thr Tyr Asn Thr Ile Ser Arg Met
370                 375                 380

Gly Gln Trp Tyr Met Ile Asp Ile Cys Leu Gly Tyr Lys Gly Lys Arg
385                 390                 395                 400

Lys Ile His Thr Val Ile Tyr Asp Ser Leu Lys Lys Leu Pro Phe Pro
                405                 410                 415

Val Lys Lys Ile Ala Lys Asp Phe Lys Leu Thr Val Leu Lys Gly Asp
                420                 425                 430

Ile Asp Tyr His Lys Glu Arg Pro Val Gly Tyr Lys Ile Thr Pro Glu
            435                 440                 445

Glu Tyr Ala Tyr Ile Lys Asn Asp Ile Gln Ile Ile Ala Glu Ala Leu
450                 455                 460

Leu Ile Gln Phe Lys Gln Gly Leu Asp Arg Met Thr Ala Gly Ser Asp
465                 470                 475                 480

Ser Leu Lys Gly Phe Lys Asp Ile Ile Thr Thr Lys Lys Phe Lys Lys
                485                 490                 495

Val Phe Pro Thr Leu Ser Leu Gly Leu Asp Lys Glu Val Arg Tyr Ala
                500                 505                 510

Tyr Arg Gly Gly Phe Thr Trp Leu Asn Asp Arg Phe Lys Glu Lys Glu
            515                 520                 525

Ile Gly Glu Gly Met Val Phe Asp Val Asn Ser Leu Tyr Pro Ala Gln
530                 535                 540

Met Tyr Ser Arg Leu Leu Pro Tyr Gly Glu Pro Ile Val Phe Glu Gly
545                 550                 555                 560

Lys Tyr Val Trp Asp Glu Asp Tyr Pro Leu His Ile Gln His Ile Arg
                565                 570                 575

Cys Glu Phe Glu Leu Lys Glu Gly Tyr Ile Pro Thr Ile Gln Ile Lys
                580                 585                 590

Arg Ser Arg Phe Tyr Lys Gly Asn Glu Tyr Leu Lys Ser Ser Gly Gly
            595                 600                 605

Glu Ile Ala Asp Leu Trp Leu Ser Asn Val Asp Leu Glu Leu Met Lys
610                 615                 620

Glu His Tyr Asp Leu Tyr Asn Val Glu Tyr Ile Ser Gly Leu Lys Phe
625                 630                 635                 640

Lys Ala Thr Thr Gly Leu Phe Lys Asp Phe Ile Asp Lys Trp Thr Tyr
                645                 650                 655

Ile Lys Thr Thr Ser Glu Gly Ala Ile Lys Gln Leu Ala Lys Arg Met
                660                 665                 670

Leu Asn Ser Leu Tyr Gly Lys Phe Ala Ser Asn Pro Asp Val Thr Gly
            675                 680                 685

Lys Val Pro Tyr Leu Lys Glu Asn Gly Ala Leu Gly Phe Arg Leu Gly
            690                 695                 700

Glu Glu Glu Thr Lys Asp Pro Val Tyr Thr Pro Met Gly Val Phe Ile
705                 710                 715                 720

Thr Ala Trp Ala Arg Tyr Thr Thr Ile Thr Ala Ala Gln Ala Cys Tyr
```

```
                725                 730                 735
Asp Arg Ile Ile Tyr Cys Asp Thr Asp Ser Ile His Leu Thr Gly Thr
            740                 745                 750

Glu Ile Pro Asp Val Ile Lys Asp Ile Val Asp Pro Lys Lys Leu Gly
        755                 760                 765

Tyr Trp Ala His Glu Ser Thr Phe Lys Arg Ala Lys Tyr Leu Arg Gln
    770                 775                 780

Lys Thr Tyr Ile Gln Asp Ile Tyr Met Lys Glu Val Asp Gly Lys Leu
785                 790                 795                 800

Val Glu Gly Ser Pro Asp Asp Tyr Thr Asp Ile Lys Phe Ser Val Lys
                805                 810                 815

Cys Ala Gly Met Thr Asp Lys Ile Lys Lys Glu Val Thr Phe Glu Asn
            820                 825                 830

Phe Lys Val Gly Phe Ser Arg Lys Met Lys Pro Lys Pro Val Gln Val
        835                 840                 845

Pro Gly Gly Val Val Leu Val Asp Asp Thr Phe Thr Ile Lys
    850                 855                 860
```

<210> SEQ ID NO 5
<211> LENGTH: 862
<212> TYPE: PRT
<213> ORGANISM: Artificial
<220> FEATURE:
<223> OTHER INFORMATION: GST, His, and S-tagged E486A-N62D mutant Phi29
      polymerase

<400> SEQUENCE: 5

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220
```

-continued

```
Gly Ser Gly His His His His His Ser Ala Gly Leu Val Pro Arg
225                 230                 235                 240

Gly Ser Thr Ala Ile Gly Met Lys Glu Thr Ala Ala Lys Phe Glu
            245                 250                 255

Arg Gln His Met Asp Ser Pro Asp Leu Gly Thr Gly Gly Ser Gly
        260                 265                 270

Asp Asp Asp Asp Lys Ser Pro Met Gly Tyr Arg Gly Ser Glu Phe Met
    275                 280                 285

Lys His Met Pro Arg Lys Met Tyr Ser Cys Asp Phe Glu Thr Thr Thr
290                 295                 300

Lys Val Glu Asp Cys Arg Val Trp Ala Tyr Gly Tyr Met Asn Ile Glu
305                 310                 315                 320

Asp His Ser Glu Tyr Lys Ile Gly Asn Ser Leu Asp Glu Phe Met Ala
            325                 330                 335

Trp Val Leu Lys Val Gln Ala Asp Leu Tyr Phe His Asp Leu Lys Phe
            340                 345                 350

Asp Gly Ala Phe Ile Ile Asn Trp Leu Glu Arg Asn Gly Phe Lys Trp
        355                 360                 365

Ser Ala Asp Gly Leu Pro Asn Thr Tyr Asn Thr Ile Ile Ser Arg Met
370                 375                 380

Gly Gln Trp Tyr Met Ile Asp Ile Cys Leu Gly Tyr Lys Gly Lys Arg
385                 390                 395                 400

Lys Ile His Thr Val Ile Tyr Asp Ser Leu Lys Lys Leu Pro Phe Pro
            405                 410                 415

Val Lys Lys Ile Ala Lys Asp Phe Lys Leu Thr Val Leu Lys Gly Asp
        420                 425                 430

Ile Asp Tyr His Lys Glu Arg Pro Val Gly Tyr Lys Ile Thr Pro Glu
    435                 440                 445

Glu Tyr Ala Tyr Ile Lys Asn Asp Ile Gln Ile Ile Ala Glu Ala Leu
            450                 455                 460

Leu Ile Gln Phe Lys Gln Gly Leu Asp Arg Met Thr Ala Gly Ser Asp
465                 470                 475                 480

Ser Leu Lys Gly Phe Lys Asp Ile Ile Thr Thr Lys Lys Phe Lys Lys
            485                 490                 495

Val Phe Pro Thr Leu Ser Leu Gly Leu Asp Lys Glu Val Arg Tyr Ala
        500                 505                 510

Tyr Arg Gly Gly Phe Thr Trp Leu Asn Asp Arg Phe Lys Glu Lys Glu
    515                 520                 525

Ile Gly Glu Gly Met Val Phe Asp Val Asn Ser Leu Tyr Pro Ala Gln
530                 535                 540

Met Tyr Ser Arg Leu Leu Pro Tyr Gly Glu Pro Ile Val Phe Glu Gly
545                 550                 555                 560

Lys Tyr Val Trp Asp Glu Asp Tyr Pro Leu His Ile Gln His Ile Arg
            565                 570                 575

Cys Glu Phe Glu Leu Lys Glu Gly Tyr Ile Pro Thr Ile Gln Ile Lys
        580                 585                 590

Arg Ser Arg Phe Tyr Lys Gly Asn Glu Tyr Leu Lys Ser Ser Gly Gly
    595                 600                 605

Glu Ile Ala Asp Leu Trp Leu Ser Asn Val Asp Leu Glu Leu Met Lys
            610                 615                 620

Glu His Tyr Asp Leu Tyr Asn Val Glu Tyr Ile Ser Gly Leu Lys Phe
625                 630                 635                 640

Lys Ala Thr Thr Gly Leu Phe Lys Asp Phe Ile Asp Lys Trp Thr Tyr
```

-continued

```
                645                 650                 655
Ile Lys Thr Thr Ser Glu Gly Ala Ile Lys Gln Leu Ala Lys Leu Met
            660                 665                 670

Leu Asn Ser Leu Tyr Gly Lys Phe Ala Ser Asn Pro Asp Val Thr Gly
        675                 680                 685

Lys Val Pro Tyr Leu Lys Glu Asn Gly Ala Leu Gly Phe Arg Leu Gly
    690                 695                 700

Glu Glu Glu Thr Lys Asp Pro Val Tyr Thr Pro Met Gly Val Phe Ile
705                 710                 715                 720

Thr Ala Trp Ala Arg Tyr Thr Thr Ile Thr Ala Ala Gln Ala Cys Tyr
                725                 730                 735

Asp Arg Ile Ile Tyr Cys Asp Thr Asp Ser Ile His Leu Thr Gly Thr
            740                 745                 750

Glu Ile Pro Asp Val Ile Lys Asp Ile Val Asp Pro Lys Lys Leu Gly
        755                 760                 765

Tyr Trp Ala His Ala Ser Thr Phe Lys Arg Ala Lys Tyr Leu Arg Gln
    770                 775                 780

Lys Thr Tyr Ile Gln Asp Ile Tyr Met Lys Glu Val Asp Gly Lys Leu
785                 790                 795                 800

Val Glu Gly Ser Pro Asp Asp Tyr Thr Asp Ile Lys Phe Ser Val Lys
                805                 810                 815

Cys Ala Gly Met Thr Asp Lys Ile Lys Lys Glu Val Thr Phe Glu Asn
            820                 825                 830

Phe Lys Val Gly Phe Ser Arg Lys Met Lys Pro Lys Pro Val Gln Val
        835                 840                 845

Pro Gly Gly Val Val Leu Val Asp Asp Thr Phe Thr Ile Lys
    850                 855                 860

<210> SEQ ID NO 6
<211> LENGTH: 862
<212> TYPE: PRT
<213> ORGANISM: Artificial
<220> FEATURE:
<223> OTHER INFORMATION: GST, His, and S-tagged E486D-N62D mutant Phi29
      polymerase

<400> SEQUENCE: 6

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65              70                  75                  80

Met Leu Gly Gly Cys Pro Lys Glu Arg Ala Glu Ile Ser Met Leu Glu
            85                  90                  95

Gly Ala Val Leu Asp Ile Arg Tyr Gly Val Ser Arg Ile Ala Tyr Ser
        100                 105                 110

Lys Asp Phe Glu Thr Leu Lys Val Asp Phe Leu Ser Lys Leu Pro Glu
    115                 120                 125

Met Leu Lys Met Phe Glu Asp Arg Leu Cys His Lys Thr Tyr Leu Asn
    130                 135                 140
```

-continued

```
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
            165                 170                 175

Val Cys Phe Lys Lys Arg Ile Glu Ala Ile Pro Gln Ile Asp Lys Tyr
        180                 185                 190

Leu Lys Ser Ser Lys Tyr Ile Ala Trp Pro Leu Gln Gly Trp Gln Ala
    195                 200                 205

Thr Phe Gly Gly Gly Asp His Pro Pro Lys Ser Asp Gly Ser Thr Ser
210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
            245                 250                 255

Arg Gln His Met Asp Ser Pro Asp Leu Gly Thr Gly Gly Gly Ser Gly
        260                 265                 270

Asp Asp Asp Asp Lys Ser Pro Met Gly Tyr Arg Gly Ser Glu Phe Met
    275                 280                 285

Lys His Met Pro Arg Lys Met Tyr Ser Cys Asp Phe Glu Thr Thr Thr
290                 295                 300

Lys Val Glu Asp Cys Arg Val Trp Ala Tyr Gly Tyr Met Asn Ile Glu
305                 310                 315                 320

Asp His Ser Glu Tyr Lys Ile Gly Asn Ser Leu Asp Glu Phe Met Ala
            325                 330                 335

Trp Val Leu Lys Val Gln Ala Asp Leu Tyr Phe His Asn Leu Lys Phe
        340                 345                 350

Asp Gly Ala Phe Ile Ile Asn Trp Leu Glu Arg Asn Gly Phe Lys Trp
    355                 360                 365

Ser Ala Asp Gly Leu Pro Asn Thr Tyr Asn Thr Ile Ile Ser Arg Met
370                 375                 380

Gly Gln Trp Tyr Met Ile Asp Ile Cys Leu Gly Tyr Lys Gly Lys Arg
385                 390                 395                 400

Lys Ile His Thr Val Ile Tyr Asp Ser Leu Lys Lys Leu Pro Phe Pro
            405                 410                 415

Val Lys Lys Ile Ala Lys Asp Phe Lys Leu Thr Val Leu Lys Gly Asp
        420                 425                 430

Ile Asp Tyr His Lys Glu Arg Pro Val Gly Tyr Lys Ile Thr Pro Glu
    435                 440                 445

Glu Tyr Ala Tyr Ile Lys Asn Asp Ile Gln Ile Ala Glu Ala Leu
450                 455                 460

Leu Ile Gln Phe Lys Gln Gly Leu Asp Arg Met Thr Ala Gly Ser Asp
465                 470                 475                 480

Ser Leu Lys Gly Phe Lys Asp Ile Ile Thr Thr Lys Lys Phe Lys Lys
            485                 490                 495

Val Phe Pro Thr Leu Ser Leu Gly Leu Asp Lys Glu Val Arg Tyr Ala
        500                 505                 510

Tyr Arg Gly Gly Phe Thr Trp Leu Asn Asp Arg Phe Lys Glu Lys Glu
    515                 520                 525

Ile Gly Glu Gly Met Val Phe Asp Val Asn Ser Leu Tyr Pro Ala Gln
530                 535                 540

Met Tyr Ser Arg Leu Leu Pro Tyr Gly Glu Pro Ile Val Phe Glu Gly
545                 550                 555                 560

Lys Tyr Val Trp Asp Glu Asp Tyr Pro Leu His Ile Gln His Ile Arg
```

```
                            565                 570                 575
    Cys Glu Phe Glu Leu Lys Glu Gly Tyr Ile Pro Thr Ile Gln Ile Lys
                    580                 585                 590

Arg Ser Arg Phe Tyr Lys Gly Asn Glu Tyr Leu Lys Ser Ser Gly Gly
                595                 600                 605

Glu Ile Ala Asp Leu Trp Leu Ser Asn Val Asp Leu Glu Leu Met Lys
        610                 615                 620

Glu His Tyr Asp Leu Tyr Asn Val Glu Tyr Ile Ser Gly Leu Lys Phe
    625                 630                 635                 640

Lys Ala Thr Thr Gly Leu Phe Lys Asp Phe Ile Asp Lys Trp Thr Tyr
                    645                 650                 655

Ile Lys Thr Thr Ser Glu Gly Ala Ile Lys Gln Leu Ala Lys Leu Met
                660                 665                 670

Leu Asn Ser Leu Tyr Gly Lys Phe Ala Ser Asn Pro Asp Val Thr Gly
                    675                 680                 685

Lys Val Pro Tyr Leu Lys Glu Asn Gly Ala Leu Gly Phe Arg Leu Gly
            690                 695                 700

Glu Glu Glu Thr Lys Asp Pro Val Tyr Thr Pro Met Gly Val Phe Ile
    705                 710                 715                 720

Thr Ala Trp Ala Arg Tyr Thr Thr Ile Thr Ala Ala Gln Ala Cys Tyr
                        725                 730                 735

Asp Arg Ile Ile Tyr Cys Asp Thr Asp Ser Ile His Leu Thr Gly Thr
                    740                 745                 750

Glu Ile Pro Asp Val Ile Lys Asp Ile Val Asp Pro Lys Lys Leu Gly
                755                 760                 765

Tyr Trp Ala His Asp Ser Thr Phe Lys Arg Ala Lys Tyr Leu Arg Gln
    770                 775                 780

Lys Thr Tyr Ile Gln Asp Ile Tyr Met Lys Glu Val Asp Gly Lys Leu
    785                 790                 795                 800

Val Glu Gly Ser Pro Asp Asp Tyr Thr Asp Ile Lys Phe Ser Val Lys
                    805                 810                 815

Cys Ala Gly Met Thr Asp Lys Ile Lys Lys Glu Val Thr Phe Glu Asn
                820                 825                 830

Phe Lys Val Gly Phe Ser Arg Lys Met Lys Pro Lys Pro Val Gln Val
                835                 840                 845

Pro Gly Gly Val Val Leu Val Asp Asp Thr Phe Thr Ile Lys
            850                 855                 860

<210> SEQ ID NO 7
<211> LENGTH: 862
<212> TYPE: PRT
<213> ORGANISM: Artificial
<220> FEATURE:
<223> OTHER INFORMATION: GST, His, and S-tagged K512A-N62D mutant Phi29
      polymerase

<400> SEQUENCE: 7

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60
```

-continued

```
Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Asp Lys Ser Pro Met Gly Tyr Arg Gly Ser Glu Phe Met
        275                 280                 285

Lys His Met Pro Arg Lys Met Tyr Ser Cys Asp Phe Glu Thr Thr Thr
    290                 295                 300

Lys Val Glu Asp Cys Arg Val Trp Ala Tyr Gly Tyr Met Asn Ile Glu
305                 310                 315                 320

Asp His Ser Glu Tyr Lys Ile Gly Asn Ser Leu Asp Glu Phe Met Ala
                325                 330                 335

Trp Val Leu Lys Val Gln Ala Asp Leu Tyr Phe His Asp Leu Lys Phe
            340                 345                 350

Asp Gly Ala Phe Ile Ile Asn Trp Leu Glu Arg Asn Gly Phe Lys Trp
        355                 360                 365

Ser Ala Asp Gly Leu Pro Asn Thr Tyr Asn Thr Ile Ile Ser Arg Met
    370                 375                 380

Gly Gln Trp Tyr Met Ile Asp Ile Cys Leu Gly Tyr Lys Gly Lys Arg
385                 390                 395                 400

Lys Ile His Thr Val Ile Tyr Asp Ser Leu Lys Lys Leu Pro Phe Pro
                405                 410                 415

Val Lys Lys Ile Ala Lys Asp Phe Lys Leu Thr Val Leu Lys Gly Asp
            420                 425                 430

Ile Asp Tyr His Lys Glu Arg Pro Val Gly Tyr Lys Ile Thr Pro Glu
        435                 440                 445

Glu Tyr Ala Tyr Ile Lys Asn Asp Ile Gln Ile Ile Ala Glu Ala Leu
    450                 455                 460

Leu Ile Gln Phe Lys Gln Gly Leu Asp Arg Met Thr Ala Gly Ser Asp
465                 470                 475                 480

Ser Leu Lys Gly Phe Lys Asp Ile Ile Thr Thr Lys Lys Phe Lys Lys
```

```
                   485               490              495
Val Phe Pro Thr Leu Ser Leu Gly Leu Asp Lys Glu Val Arg Tyr Ala
                500               505              510

Tyr Arg Gly Gly Phe Thr Trp Leu Asn Asp Arg Phe Lys Glu Lys Glu
            515               520              525

Ile Gly Glu Gly Met Val Phe Asp Val Asn Ser Leu Tyr Pro Ala Gln
        530               535              540

Met Tyr Ser Arg Leu Leu Pro Tyr Gly Glu Pro Ile Val Phe Glu Gly
545               550              555              560

Lys Tyr Val Trp Asp Glu Asp Tyr Pro Leu His Ile Gln His Ile Arg
                565               570              575

Cys Glu Phe Glu Leu Lys Glu Gly Tyr Ile Pro Thr Ile Gln Ile Lys
            580               585              590

Arg Ser Arg Phe Tyr Lys Gly Asn Glu Tyr Leu Lys Ser Ser Gly Gly
        595               600              605

Glu Ile Ala Asp Leu Trp Leu Ser Asn Val Asp Leu Glu Leu Met Lys
    610               615              620

Glu His Tyr Asp Leu Tyr Asn Val Glu Tyr Ile Ser Gly Leu Lys Phe
625               630              635              640

Lys Ala Thr Thr Gly Leu Phe Lys Asp Phe Ile Asp Lys Trp Thr Tyr
                645               650              655

Ile Lys Thr Thr Ser Glu Gly Ala Ile Lys Gln Leu Ala Lys Leu Met
            660               665              670

Leu Asn Ser Leu Tyr Gly Lys Phe Ala Ser Asn Pro Asp Val Thr Gly
        675               680              685

Lys Val Pro Tyr Leu Lys Glu Asn Gly Ala Leu Gly Phe Arg Leu Gly
    690               695              700

Glu Glu Glu Thr Lys Asp Pro Val Tyr Thr Pro Met Gly Val Phe Ile
705               710              715              720

Thr Ala Trp Ala Arg Tyr Thr Thr Ile Thr Ala Ala Gln Ala Cys Tyr
                725               730              735

Asp Arg Ile Ile Tyr Cys Asp Thr Asp Ser Ile His Leu Thr Gly Thr
            740               745              750

Glu Ile Pro Asp Val Ile Lys Asp Ile Val Asp Pro Lys Lys Leu Gly
        755               760              765

Tyr Trp Ala His Glu Ser Thr Phe Lys Arg Ala Lys Tyr Leu Arg Gln
    770               775              780

Lys Thr Tyr Ile Gln Asp Ile Tyr Met Lys Glu Val Asp Gly Ala Leu
785               790              795              800

Val Glu Gly Ser Pro Asp Asp Tyr Thr Asp Ile Lys Phe Ser Val Lys
                805               810              815

Cys Ala Gly Met Thr Asp Lys Ile Lys Lys Glu Val Thr Phe Glu Asn
            820               825              830

Phe Lys Val Gly Phe Ser Arg Lys Met Lys Pro Lys Pro Val Gln Val
        835               840              845

Pro Gly Gly Val Val Leu Val Asp Asp Thr Phe Thr Ile Lys
    850               855              860

<210> SEQ ID NO 8
<211> LENGTH: 7667
<212> TYPE: DNA
<213> ORGANISM: Artificial
<220> FEATURE:
<223> OTHER INFORMATION: plasmid encoding N62D mutant Phi29 polymerase
```

<400> SEQUENCE: 8

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tcccttagg       180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta tagggatttt tgccgatttc ggcctattgg ttaaaaaatg agctgattta     420
acaaaatttt aacgcgaatt ttaacaaaat attaacgttt acaatttcag gtggcacttt     480
tcggggaaat gtgcgcggaa cccctatttg tttattttc taaatacatt caaatatgta      540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa ataaggtta tcaagtgaga      780
aatcaccatg agtgacgact gaatccggtg agaatggcaa aagtttatgc atttctttcc    840
agacttgttc aacaggccag ccattacgct cgtcatcaaa atcactcgca tcaaccaaac     900
cgttattcat tcgtgattgc gcctgagcga acgaaatac gcgatcgctg ttaaaaggac      960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccgggttg gactcaagac gatagttacc ggataaggcg     1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
```

```
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgctagtca tgccccgcgc   3180
ccaccggaag gagctgactg ggttgaaggc tctcaagggc atcggtcgag atcccggtgc   3240
ctaatgagtg agctaactta cattaattgc gttgcgctca ctgcccgctt tccagtcggg   3300
aaacctgtcg tgccagctgc attaatgaat cggccaacgc gcggggagag gcggtttgcg   3360
tattgggcgc cagggtggtt tttcttttca ccagtgagac gggcaacagc tgattgccct   3420
tcaccgcctg gccctgagag agttgcagca agcggtccac gctggtttgc cccagcaggc   3480
gaaaatcctg tttgatggtg gttaacggcg ggatataaca tgagctgtct tcggtatcgt   3540
cgtatcccac taccgagatg tccgcaccaa cgcgcagccc ggactcggta atggcgcgca   3600
ttgcgcccag cgccatctga tcgttggcaa ccagcatcgc agtgggaacg atgccctcat   3660
tcagcatttg catggtttgt tgaaaaccgg acatggcact ccagtcgcct tcccgttccg   3720
ctatcggctg aatttgattg cgagtgagat atttatgcca gccagccaga cgcagacgcg   3780
ccgagacaga acttaatggg cccgctaaca gcgcgatttg ctggtgaccc aatgcgacca   3840
gatgctccac gcccagtcgc gtaccgtctt catgggagaa aataatactg ttgatgggtg   3900
tctggtcaga gacatcaaga aataacgccg gaacattagt gcaggcagct tccacagcaa   3960
tggcatcctg gtcatccagc ggatagttaa tgatcagccc actgacgcgt tgcgcgagaa   4020
gattgtgcac cgccgcttta caggcttcga cgccgcttcg ttctaccatc gacaccacca   4080
cgctggcacc cagttgatcg gcgcgagatt taatcgccgc gacaatttgc gacggcgcgt   4140
gcagggccag actggaggtg gcaacgccaa tcagcaacga ctgtttgccc gccagttgtt   4200
gtgccacgcg gttgggaatg taattcagct ccgccatcgc cgcttccact ttttcccgcg   4260
ttttcgcaga acgtggctg gcctggttca ccacgcggga aacggtctga taagagacac   4320
cggcatactc tgcgacatcg tataacgtta ctggtttcac attcaccacc ctgaattgac   4380
tctcttccgg cgctatcat gccataccgc gaaaggtttt gcgccattcg atggtgtccg   4440
ggatctcgac gctctccctt atgcgactcc tgcattagga agcagcccag tagtaggttg   4500
aggccgttga gcaccgccgc cgcaaggaat ggtgcatgca aggagatggc gcccaacagt   4560
cccccggcca cggggcctgc caccatacc acgccgaaac aagcgctcat gagcccgaag   4620
tggcgagccc gatcttcccc atcggtgatg tcggcgatat aggcgccagc aaccgcacct   4680
```

```
gtggcgccgg tgatgccggc cacgatgcgt ccggcgtaga ggatcgagat cgatctcgat    4740
cccgcgaaat taatacgact cactataggg gaattgtgag cggataacaa ttcccctcta    4800
gaaataattt tgtttaactt taagaaggag atatacatat gtcccctata ctaggttatt    4860
ggaaaattaa gggccttgtg caacccactc gacttctttt ggaatatctt gaagaaaaat    4920
atgaagagca tttgtatgag cgcgatgaag gtgataaatg gcgaaacaaa aagtttgaat    4980
tgggtttgga gtttcccaat cttccttatt atattgatgg tgatgttaaa ttaacacagt    5040
ctatggccat catacgttat atagctgaca agcacaacat gttgggtggt tgtccaaaag    5100
agcgtgcaga gatttcaatg cttgaaggag cggttttgga tattagatac ggtgtttcga    5160
gaattgcata tagtaaagac tttgaaactc tcaaagttga ttttcttagc aagctacctg    5220
aaatgctgaa aatgttcgaa gatcgtttat gtcataaaac atatttaaat ggtgatcatg    5280
taacccatcc tgacttcatg ttgtatgacg ctcttgatgt tgttttatac atggacccaa    5340
tgtgcctgga tgcgttccca aaattagttt gttttaaaaa acgtattgaa gctatcccac    5400
aaattgataa gtacttgaaa tccagcaagt atatagcatg gcctttgcag ggctggcaag    5460
ccacgtttgg tggtggcgac catcctccaa aatcggatgg ttcaactagt ggttctggtc    5520
atcaccatca ccatcactcc gcgggtctgg tgccacgcgg tagtactgca attggtatga    5580
aagaaaccgc tgctgctaaa ttcgaacgcc agcacatgga cagcccagat ctgggtaccg    5640
gtggtggctc cggtgatgac gacgacaaga gtccctgggg atatcgggga tccgaattca    5700
tgaagcatat gccgagaaag atgtatagtt gtgactttga acaactact aaagtggaag    5760 actgtagggt atgggcgtat ggttatatga atatagaaga tcacagtgag tacaaaatag    5820
gtaatagcct ggatgagttt atggcgtggg tgttgaaggt acaagctgat ctatatttcc    5880
atgatctcaa atttgacgga gcttttatca ttaactggtt ggaacgtaat ggttttaagt    5940
ggtcggctga cggattgcca aacacatata atacgatcat atctcgcatg ggacaatggt    6000
acatgattga tatatgttta ggctacaaag ggaaacgtaa gatacataca gtgatatatg    6060
acagcttaaa gaaactaccg tttcctgtta agaagatagc taaagacttt aaactaactg    6120
ttcttaaagg tgatattgat taccacaaag aaagaccagt cggctataag ataacacccg    6180
aagaatacgc ctatattaaa aacgatattc agattattgc ggaagctctg ttaattcagt    6240
ttaagcaagg tttagaccgg atgacagcag gcagtgacag tctaaaaggt tcaaggata    6300 ttataaccac taagaaattc aaaaaggtgt ttcctacatt gagtcttgga ctcgataagg    6360
aagtgagata cgcctataga ggtggtttta catggttaaa tgataggttc aaagaaaaag    6420
aaatcggaga aggcatggtc ttcgatgtta atagtctata tcctgcacag atgtatagtc    6480
gtctccttcc atatggtgaa cctatagtat tcgagggtaa atacgtttgg gacgaagatt    6540
acccactaca catacagcat atcagatgtg agttcgaatt gaaagagggc tatataccca    6600
ctatacagat aaaagaagt aggttttata aaggtaatga gtacctaaaa agtagcggcg    6660
gggagatagc cgacctctgg ttgtcaaatg tagacctaga attaatgaaa gaacactacg    6720
atttatataa cgttgaatat atcagcggct taaaatttaa agcaactaca ggtttgttta    6780
aagattttat agataaatgg acgtacatca agacgacatc agaaggagcg atcaagcaac    6840
tagcaaaact gatgttaaac agtctatacg gtaaattcgc tagtaaccct gatgttacag    6900
ggaaagtccc ttatttaaaa gagaatgggg cgctaggttt cagacttgga gaagaggaaa    6960
caaaagaccc tgtttataca cctatgggcg ttttcatcac tgcatgggct agatacacga    7020
caattacagc ggcacaggct tgttatgatc ggataatata ctgtgatact gacagcatac    7080
```

-continued

```
atttaacggg tacagagata cctgatgtaa taaaagatat agttgaccct aagaaattgg      7140
gatactgggc acatgaaagt acattcaaaa gagctaaata tctgagacag aagacctata      7200
tacaagacat ctatatgaaa gaagtagatg gtaagttagt agaaggtagt ccagatgatt      7260
acactgatat aaaatttagt gttaaatgtg cgggaatgac tgacaagatt aagaaagagg      7320
ttacgtttga gaatttcaaa gtcggattca gtcggaaaat gaagcctaag cctgtgcaag      7380
tgccgggcgg ggtggttctg gttgatgaca cattcacaat caaataagaa ttctgtacag      7440
gccttggcgc gcctgcaggc gagctccgtc gacaagcttg cggccgcact cgagcaccac      7500
caccaccacc accaccacta attgattaat acctaggctg ctaaacaaag cccgaaagga      7560
agctgagttg gctgctgcca ccgctgagca ataactagca taaccccttg gggcctctaa      7620
acgggtcttg aggggttttt tgctgaaagg aggaactata tccggat                   7667
```